(12) United States Patent
Hasserodt et al.

(10) Patent No.: US 9,605,296 B2
(45) Date of Patent: Mar. 28, 2017

(54) FLUOROGENIC PEPTIDASE SUBSTRATE

(71) Applicants: ECOLE NORMALE SUPERIEURE DE LYON, Lyons (FR); CENTRE NATIONAL DE LA RECHERCHE SCIENTIFIQUE, Paris (FR)

(72) Inventors: Jens Hasserodt, Lyons (FR); Oliver Thorn-Seshold, Lyons (FR)

(73) Assignees: ECOLE NORMALE SUPERIEURE DE LYON, Lyons (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 177 days.

(21) Appl. No.: 14/347,783

(22) PCT Filed: Sep. 27, 2012

(86) PCT No.: PCT/FR2012/052196
§ 371 (c)(1),
(2) Date: Mar. 27, 2014

(87) PCT Pub. No.: WO2013/045854
PCT Pub. Date: Apr. 4, 2013

(65) Prior Publication Data
US 2014/0234887 A1 Aug. 21, 2014

(30) Foreign Application Priority Data

Sep. 29, 2011 (FR) .................................... 11 58732

(51) Int. Cl.
| | | |
|---|---|---|
| *C12Q 1/37* | (2006.01) | |
| *C07D 403/12* | (2006.01) | |
| *C07D 401/12* | (2006.01) | |
| *C07D 239/91* | (2006.01) | |
| *G01N 33/542* | (2006.01) | |
| *C07D 417/14* | (2006.01) | |
| *C07K 5/113* | (2006.01) | |

(52) U.S. Cl.
CPC ............ *C12Q 1/37* (2013.01); *C07D 239/91* (2013.01); *C07D 401/12* (2013.01); *C07D 403/12* (2013.01); *C07D 417/14* (2013.01); *G01N 33/542* (2013.01); *C07K 5/1021* (2013.01)

(58) Field of Classification Search
CPC .. C07D 401/12; C07D 417/14; C07D 239/91; C07D 403/12; G01N 33/542; C07K 5/1021; C12Q 1/37
See application file for complete search history.

(56) References Cited

U.S. PATENT DOCUMENTS 5,316,906 A   5/1994   Haugland et al.
7,626,042 B2  12/2009  Muto et al.

2003/0059847 A1  3/2003  Backes et al.
2003/0096743 A1  5/2003  Senter et al.
2010/0041748 A1  2/2010  Milne et al.

FOREIGN PATENT DOCUMENTS

| EP | 2 266 963 | 12/2010 |
|---|---|---|
| WO | 2007/140272 | 12/2007 |
| WO | 2008/145830 | 12/2008 |
| WO | 2008/152305 | 12/2008 |
| WO | 2008/152306 | 12/2008 |
| WO | 2012/122420 | 9/2012 |
| WO | 2012/122422 | 9/2012 |

OTHER PUBLICATIONS

Thorn-Seshold, O., "A robust, high-sensitivity stealth probe for peptidases." Chemical Communications 48.50 (2012): 6253-6255.*
Y. Meyer et al., "A Comparative study . . . fluorogenic probes", Organic & Biomolecular Chemistry, 2010, 8, pp. 1777-1780.
C. Fahrni et al., "Excited-State Intramolecular . . . 2-(2'-Tosylaminophenyl)benzimidazole", J. Phys. Chem. A., 2002, 106, pp. 7655-7663.
S. Santra et al., "Excited-State Intramolecular . . . 2-(2'-Acetamidophenyl)benzimidazole", J. Phys. Chem. A, 2000, 104, pp. 476-482.
D. Williams et al., "Intramolecular Proton . . . Fluorescent Compounds", The Journal of Physical Chemistry, vol. 74, pp. 4473-4480, 1970.
Toki et al., "Protease-Mediated . . . Anticancer Prodrugs", J. Org. Chem. 2002, 37, pp. 1866-1872.
W. Saari et al., "Cyclization-Activated . . . 4-Hydroxyanisole", Journal of Medicinal Chemistry (1990) 33, pp. 97-101.
Carl et al., "A Novel Connector . . . Prodrug Design", Journal of Medicinal Chemistry, vol. 24, No. 5, May 1981, pp. 479-480.
C. Kragelund et al., "Ecophysiology of the . . . in acvtivated sludge", FEMS Microbiology Ecology 54 (2005), pp. 111-122.
Zhang et al., "An Autoimmolative Spacer . . . for Acyl Hydrolases", Chemistry, Euro. J. 2010, 16, pp. 792-795.
J.K. Dey et al., "Solvatochromism and . . . 2-(Aminophenyl)benzothiazoles", The Chemical Society of Japan, 1991, vol. 64, No. 10, pp. 3142-3152.
Cellier et al., "2-Arylbenzothiazole, . . . important bacteria", Bioorganic & Medicinal Chemistry, 19 (2011), pp. 2903-2910.

(Continued)

*Primary Examiner* — Samantha Shterengarts
*Assistant Examiner* — Matt Mauro
(74) *Attorney, Agent, or Firm* — Clark & Brody

(57) ABSTRACT

The invention relates to novel peptidase substrates of formula (I):

$$R_0 \underset{H}{\overset{R_1}{\diagup}} N \underset{n}{\diagup} \overset{R_2 \; R_3}{\diagup} \underset{R_4}{\overset{O}{\diagup}} N \diagup R_5$$

wherein $R_0$, $R_1$, $R_2$, $R_3$, $R_4$, $R_5$ and n are as defined in claim 1,
and a method for detecting the presence of a catalytically active peptidase, by means of one of these substrates.

14 Claims, 4 Drawing Sheets

(56) References Cited

OTHER PUBLICATIONS

Richard et al., "Latent Fluorophores . . . Protease Sensing", Bioconjugate Chemistry (2008), 19, pp. 1707-1718.

M. Wakselman, "1,4- and 1,6-Elimination . . . Biochemical Applications", New Journal of Chemistry (1983), 7, pp. 439-447.

M. Waibel et al., "Efficient synthesis . . . -4(3H)-ones", Tetrahedron Letters 50 (2009) pp. 2767-2769.

Ormson et al., "Excited State . . . to Nitrogen", Progress in Reaction Kinetics (1994), vol. 19, pp. 45-91.

Boonacker et al., "Enzyme Cytochemical . . . to Proteolysis", The Journal of Histochemistry & Cytochemistry, vol. 49(12); 1473-1486, 2001.

Diwu et al., "Spectral Properties . . . Activity Sites", SPIE Advances in Fluorescence Sensing Technology IV (1999), 3602, 265-274.

K. Kuldova et al., "Excited state . . . related compounds", Journal of Luminescence 72-74 (1997) pp. 513-514.

D. Le Gourrierec et al., "Excited State . . . to Oxygen", Progress in Reaction Kinetics, vol. 19, pp. 211-275, 1994.

* cited by examiner

FLUOROGENIC PEPTIDASE SUBSTRATE

The invention relates to the technical field of probes for detecting enzymatic activity. In particular, the invention relates to novel fluorogenic substrates for detecting the presence of a catalytically active peptidase and to a detection method using such substrates.

In the analysis of a biological or chemical sample, detection of peptidase (or protease) activity may be very useful (Boonacker E. and Van Noorden C. J. F. J. Histochem. Cytochem. (2001) 49, 1473-1486). Entire organisms, cells or cell extracts, biological liquids or chemical mixtures are examples of biological or chemical samples in which peptidase activity may be detected. Exo- and endoproteases are a vast family of enzymes which includes many biomarkers of diverse pathologies. They are also involved in many benign cell processes and are therefore the subject of countless studies on behalf of cell biologists. Thus, their detection may give information relating to a particular metabolic or morbid condition, for example.

Consequently, a probe capable of detecting peptidase activity is very useful. Detection of this activity by capture of fluorescence light is a much more sensitive method than collecting the remainder of white light during simple absorption by the probe, i.e. the detection threshold is much lower. The detection of a fluorescence emission is very easy to apply, so that fluorescent probes are very attractive tools for life sciences. For example, the class of fluorophores leading to an intramolecular proton transfer in an excited state, called ESIPT (Excited State Intramolecular Proton Transfer), is described in a) Ormson, S. M., et al. Progress in Reaction Kinetics (1994) 19, 45-91; and in b) Legourrierec, D., et al. Progress in Reaction Kinetics (1994), 19, 211-275). The first interpretation of high fluorescence found in certain phenolic compounds as being an ESIPT phenomenon may be ascribed to Weller (for methyl salicylate: Weller, A. (1961). Fast Reactions of Excited Molecules. Progress in Reaction Kinetics and Mechanism 1, 187), and to Heller and Williams (for hydroxyphenylbenzoxazoles: Heller A., and Williams, D. L., J. Phys. Chem. (1970) 74, 4473-4480).

The class of ESIPT fluorophores is particularly attractive for the researcher in life sciences, because of its exceptional properties as compared with conventional fluorophores. The exceptional properties of ESIPT fluorophores are:
   (a) a large Stokes shift often exceeding 130 nm and capable of attaining values of 250 nm which allows instrumental selections which maximize detection sensitivity;
   (b) excellent resistance to photo-bleaching with levels which may be greater by several orders of magnitude to those of model fluorophores like fluorescein;
   (c) the possibility of designing fluorophores which emit bright fluorescence in the solid state, a rare property among all the known fluorophores. The latter performance allows for production of a high intensity signal at the site of activation of the probe, with minimum dilution caused by diffusion; and finally,
   (d) the possibility of designing ESIPT phenolic fluorophores which emit in the red or the near infrared (600 to 850 nm) where transparence of the fabrics is the highest; the corresponding probe would particularly be suitable for imaging in living animals.

The majority of these properties if such a fluorophore was integrated into a probe, would form a significant contribution as compared with the properties of conventional marketed probes which are hindered in their performances by small Stokes shifts and medium to high photo-bleaching, and which lead without any exception to fluorophores in the state of a solution.

Within the scope of the invention, the inventors were interested in a suitable choice of a unit which may be cleaved by an enzyme which would give the complete probe, incorporating an ESIPT fluorophore as described above, total water-solubility, a pre-requisite condition for attaining the site and the tissues of interest. Such a probe would allow a significant increase in detection sensitivity, which, for its part, would allow reduction of the dose and thus may notably be adapted to an in vivo imaging application, while reducing the problems of toxicity. The sensitivity level is closely related (i) to the photo-bleaching level, (ii) to the accumulation level of the fluorescent signal on its production site (and therefore to the diffusion rate from this site, and to the question of knowing whether the fluorophore precipitates or not) (iii) to the real on/off mode in which the probe operates (absence of a false positive signal due to spontaneous hydrolysis of the probe), and (iv) to the superposition level of the excitation spectrum and of the emission spectrum (their separation at the base line being the most favorable configuration; see point (a) above). Point (iv) has a most particular importance, since the complete separation at the base line provides the opportunity of a very wide selection of filters for the light source (for exciting the molecule at all possible wave lengths), but still more importantly, for the detector (for collecting photons from all the wavelengths emitted by the fluorophore). Point (iv) also minimizes the perturbation of the detection process by tissue self-fluorescence (characterized by a small Stokes shift of natural fluorophores), a recurrent problem encountered with established fluorophores, which themselves also have a small Stokes shift.

During recent years, there has been growing interest in the design of enzyme substrates with three triggering/binding agents/fluorophore components by using spacers with self-immolation as a binding agent. Among the important class of ESIPT fluorophores, 2-hydroxyphenylquinazolinone (HPQ) is of particular interest, given that it is perfectly insoluble in aqueous/physiological media, while being strongly fluorescent in the solid state and only in the solid state. Nevertheless, it is very difficult to use HPQ in the design of a molecular probe which gives information on the activity of an acyl hydrolase (esterase or peptidase). Moreover, the main activities for which a probe based on HPQ has already been designed (and marketed) are those of phosphatases and glycosidases, because of the impossibility of generating a stable probe based on HPQ with an acylated phenolic hydroxyl since the resulting product is prone to rapid spontaneous hydrolysis which, of course, releases free insoluble HPQ and thus produces an erroneous fluorescent signal (false positive signal). It should also be noted that the marketing by Molecular Probes of such acylated compounds (ELF97 esterase substrate (ELF97 acetate) and ELF97 lipase substrate (ELF97 palmitate)) was interrupted in 2005 and their study by certain researchers went unheeded (C. Kragelund et al./FEMS Microbiology Ecology 54 (2005) 111-122). The reason is the intrinsic instability to hydrolysis of phenolic esters, in particular ESIPT phenolic esters, a fact which is further worsened by the anti-chimeric assistance to hydrolysis on behalf of an internal nucleophilic agent (the nitrogen of the imine).

Another solution was contemplated by other teams for getting rid of this self-degradation: the switching to an ESIPT fluorophore derived from HPQ which has an amino group instead of an hydroxy group. This solution was contemplated since it is known that the corresponding acylated compound which gives a carboximide bond instead of a carboxylic ester, is not very likely to undergo spontaneous hydrolysis any longer: (a) Marie Cellier, Olivier J. Fabrega, Elizabeth Fazackerley, Arthur L. James, Sylvain Orenga, John D. Perry, Vindhya L. Salwatura, Stephen P. Stanforth, Bioorganic & Medicinal Chemistry 19 (2011) 2903-2910, title: "2-Arylbenzothiazole, benzoxazole and benzimidazolederivatives as fluorogenic substrates for the detection of nitroreductase and aminopeptidase activity in clinically important bacteria"; (b) Fabrega, O.; James, A.; Salwatura, V. L.; Orenga, S.; Stanforth, S. P. Patent WO2008152305; and Fabrega, O.; James, A.; Salwatura, V. L.; Orenga, S.; Stanforth, S. P. Patent WO2008152306.

Now, this approach has the following drawbacks:

the compounds resembling a fluorophore capable of exhibiting the ESIPT effect and comprising an aniline unit instead of a phenol unit (as present in HPQ) hardly show any ESIPT band characterized by a large Stokes shift. In the best of cases, these fluorophores behave like "normal" fluorophores with a small Stokes shift, therefore with an emission wavelength close to the excitation one. The following authors then state that such compounds are "non-fluorescent" or "not exhibiting ESIPT fluorescence": (a) J. K. Dey; S. K. Dogra, Bull. Chem. Soc. Jpn. 1991, 64, 3142-3152; (b) K. Kuldov, Y. Eichen, P. Emele, H. P. Trommsdorff, Journal of Luminescence 72-74 (1997) 513-514. This phenomenon of an absence of ESIPT fluorescence of the "aniline" analogues as compared with HPQ was also demonstrated in the range of "quinazolinones" by one of the inventors of the present patent application: Michael Waibel, Jens Hasserodt, Tetrahedron Letters 50 (2009) 2767-2769. The benefit of working with quinazolinones (=>HPQ) instead of benzo-thiazoles, -oxazoles or -imidazoles is based on the superior insolubility of quinazolinones, which therefore leads to a maximization of the signal instead of the precipitation of the fluorophore following its transformation by the target enzyme. This maximum insolubility was ascribed to the dimerization phenomenon via two intermolecular hydrogen bonds between the lactam units in the crystal lattice of the precipitated product (Diwu, Z.; Klaubert, D. H.; Haugland, R. P., SPIE Advances in Fluorescence Sensing Technology IV (1999), 3602, 265-274).

the compounds resembling a fluorophore capable of exhibiting the ESIPT effect and comprising an aniline unit (2-aminophenyl) for which the amino group is acylated (S. Santra et al., J. Phys. Chem. A 2000, 104, 476-482) or sulfonylated (Christoph J. Fahrni et al., J. Phys. Chem. A 2002, 106, 7655-7663), and which therefore include an electron attractor group and always have a hydrogen atom on the nitrogen atom, exhibit high intensity ESIPT fluorescence as compared with the non-acylated derivative. A probe which has such a group and which targets a peptidase should thus rather exhibit an "on=>off" operating mode, a mode which is not very attractive since it is difficult to determine if a decrease in the intensity of the signal corresponds to conversion or to simple diffusion of the initial probe.

In 2010, one of the inventors of the present patent application also described in Chem. Eur. 1 (2010), 16, 792-795, an enzyme substrate with three components: peptide sequence/spacer/HPQ wherein the spacer includes an acylated O,O-acetal group bound to HPQ. Although the studied probe is relatively stable under physiological conditions, it however has a residual degradation rate leading to a false positive fluorescent signal in cell imaging applications.

Solutions leading to a more pronounced or even complete absence of spontaneous degradation of the probes and therefore of a production of erroneous signals, a fundamental preliminary condition for their use in vitro and in vivo applications were proposed with the use of a para-amino benzyl spacer grafted on the phenolic fluorophore (WO2068145830, Richard, J. A., et al. Bioconjugate Chemistry (2008) 19, 1707-1718). Although such para-aminobenzyl spacers have already been used in the design of pro-drugs since the beginning of the 80s (Wakselman, M. New Journal of Chemistry (1983), 7, 439-447; Carl, P. L., et al. Journal of Medicinal Chemistry (1981) 24, 479-480; Toki, B. E., et al. Journal of Organic Chemistry (2002) 67, 1866-1872; and Senter, US2003096743), they have a known major drawback: the use of para-aminobenzyl spacers (or of their oxygenated analogues) in artificial enzyme substrates leads to permanent alkylation of the protein, often near or inside the catalytic site. This negative property was subsequently advantageously used in many articles which have proposed substrates which inactivate the enzymes, i.e. leading to an enzyme which is no longer capable of further converting the substrate molecules, as shown in the following Scheme 1.

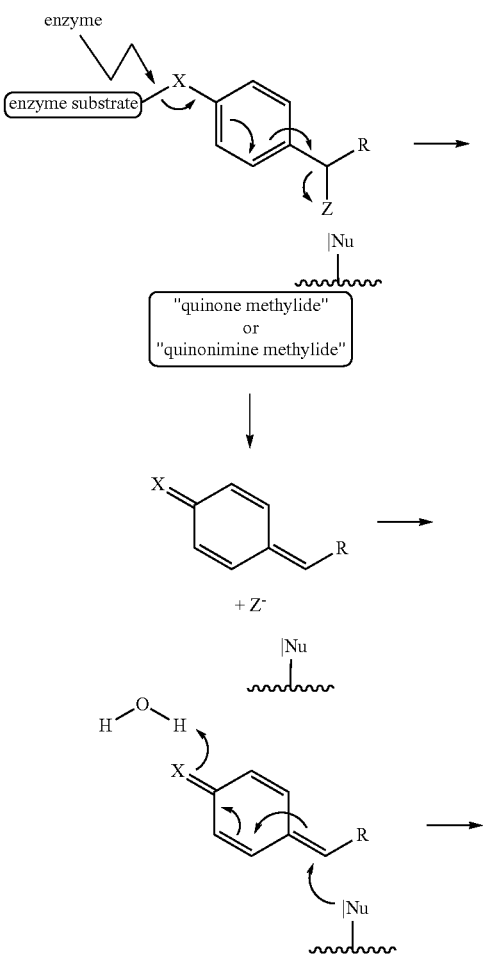

Scheme 1

-continued

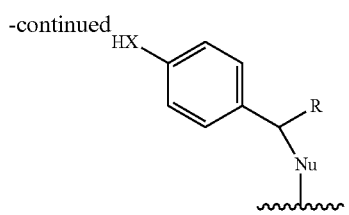

X = N, O; Z = leaving group: Nu: nucleophilic agent on the enzyme

Different work on the enzymatic marking with enzyme substrates based on ortho- or para-amino- (or hydroxy-) benzyl shows that quinonimine methylides are highly reactive species which alkylate the nucleophilic agents and which risk randomly modifying the molecular properties of the bio-macromolecules which are in their close vicinity. The activation or the reduced catalytic capabilities of the target enzyme are, of course, highly detrimental to the sensitivity of imaging experiments using such a fluorogenic probe, since the enzymatic amplification is lost. Except for direct inactivation of the target enzyme, random alkylation of the surface of this protein or of any other neighboring protein also has the risk of an immune response. Both cases generate limited tolerance on behalf of the respective organism and therefore high toxicity for the latter.

In this context, the applicant proposed to provide other spacers 1) which would allow creation of a stable probe incorporating an ESIPT fluorophore, with thus a minimization of the background fluorescence of the non-transformed probe, and 2) which would not have the same risks in terms of toxicity as the amino benzyl spacer described in the state of the art. The applicant was interested in diamine spacers. Diamine spacers, as a portion of a tertiary phenolic carbamate were used previously for creating prodrugs which may be transformed into an active drug, following transformation by a specific target enzyme. It is well known in the field of designing prodrugs that phenolic aminoethyl carbamates are sacrificed at appreciable levels, under physiological conditions, only if the two amines are secondary amines, i.e. are each dually alkylated, as shown by Scheme 2 below (Saari, W. S., et al. Journal of Medicinal Chemistry (1990) 33, 97-101).

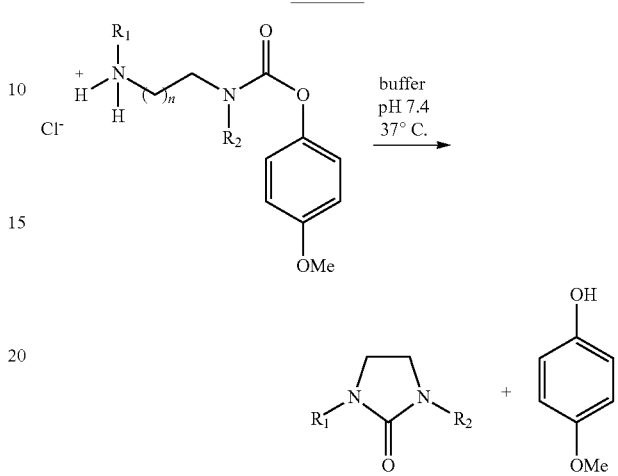

Scheme 2

| n | $R_1$ | $R_2$ | $t_{1/2}$ (min) |
|---|-------|-------|-----------------|
| 1 | Me    | Me    | 36              |
| 1 | Et    | Et    | 118             |
| 1 | Me    | H     | 304             |
| 1 | H     | Me    | 335             |
| 1 | H     | H     | 724             |
| 2 | H     | H     | 910             |
| 2 | Me    | Me    | 942             |

The experimental results described in application WO2007/140272 on the design of prodrugs clearly show the detrimental impact on the sacrificial level of the spacer, when the distal amine is a primary (only one alkyl substituent) and non-secondary amine. The resulting conversion levels are shown in the following Scheme 3.

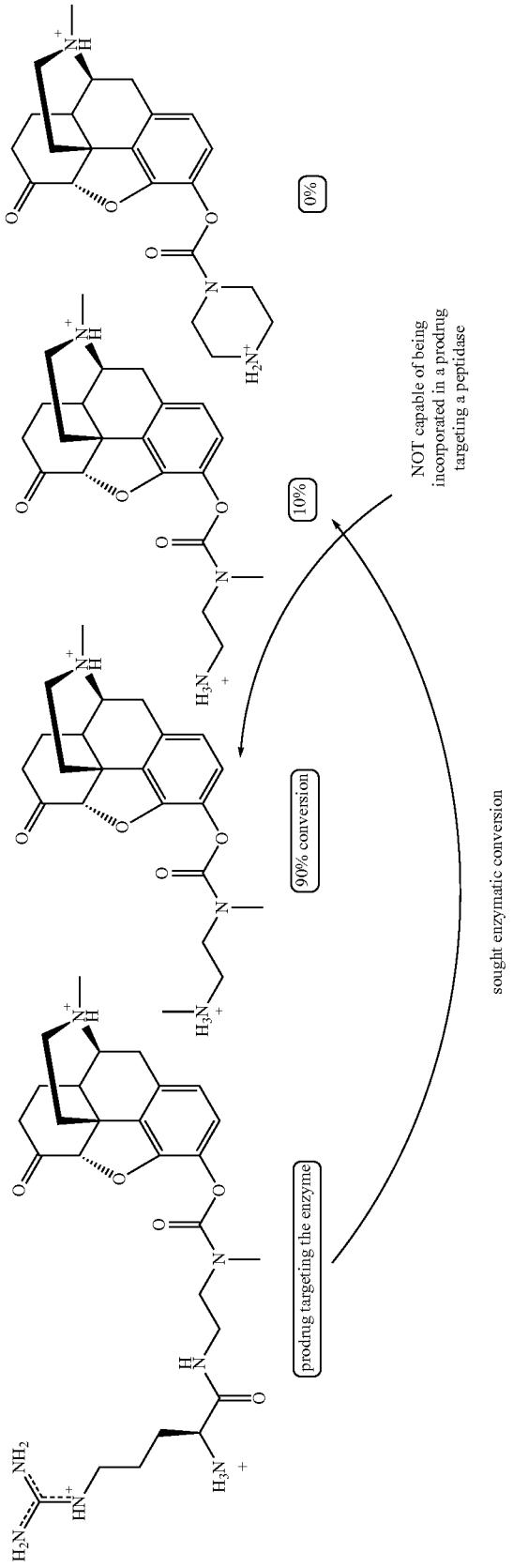

While the structure with two secondary amines is sacrificed in an amount of 90% of free phenol in 24 hours in physiological media, the structure with a primary amine and a secondary amine (being part of a tertiary carbamate) is only converted in an amount of 10% under these conditions.

A significant point, which is underlined in patent application WO2007/142172, is that the spacer with two secondary amines (a conversion of 90% if it is subject to physiological conditions) is not useful for incorporation in a prodrug targeting a peptidase since most peptidases (or amidases) do not recognize tertiary peptide bonds. This fact which has been established for a long time, was confirmed by a very recent study, on the release of phenolic fluorophores by probes targeting profluorescent peptidases (Meyer, Y., et al. OrgBiomolChem (2010) 8, 1777-1780).

In this context, the object of the invention is to propose novel substrates of peptidases which are stable in an aqueous medium and which remain non-fluorescent or weakly fluorescent at a wavelength quite different from the one at which the released fluorophore is itself fluorescent, but which react with peptidases for producing a small fluorescent molecule based on ESIPT such as HPQ. According to the invention, it is contemplated to propose a peptidase substrate having the following properties:
  specificity for a particular peptidase,
  absence of any false positive signal produced by spontaneous degradation of the probe, in particular as compared with probes having O,O acetal spacers,
  good sacrificial kinetics,
  biocompatibility without the identified toxicity which is associated with the use of aminobenzyl spacers.

More specifically, the invention relates to a peptidase substrate of formula (I):

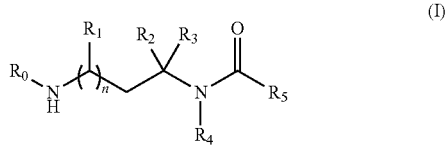

wherein:
$R_0$ is a peptidyl or aminoacid group bound to the NH group via its carboxy-terminal end,
n is equal to 0 or 1,
$R_1$ is a hydrogen atom or a side chain of an amino acid,
$R_5$ is a phenoxy derivative, the corresponding phenol derivative of which belongs to the class of ESIPT fluorophores,
$R_2$, $R_3$ and $R_4$ are defined as follows:
  Either $R_2$ is a $(C_1$-$C_4)$alkyl or a hydrogen atom, $R_3$ is a $(C_1$-$C_4)$alkyl and $R_4$ is a $(C_1$-$C_4)$alkyl,
  or $R_2$ is a $(C_1$-$C_4)$alkyl or a hydrogen atom and $R_3$ and $R_4$ are bound together and form with the carbon and nitrogen atoms to which they are bound, an aliphatic heterocycle, this heterocycle may be substituted with a group, of the ammonium carboxylate or sulfonate type, allowing an increase in the water-solubility of the substrate,
  or $R_4$ is a $(C_1$-$C_4)$alkyl and $R_2$ and $R_3$ are bound together and form with the carbon atoms to which they are bound, an aliphatic carbocycle,
in the form of a mixture of optical isomers or diastereoisomers according to all proportions, or in a form enriched with an optical isomer or with a diastereoisomer.

The substrate according to the invention acts like a molecular probe capable of revealing the presence of specific enzymatic activity by detection of fluorescence. More specifically, the probe is invisible before encountering the targeted enzyme, (i.e. a "stealth probe"), but when it is chemically modified by said enzyme, it fragments via a cascade reaction for producing intense fluorescence. The probe consists of three molecular components i) a smart spacer which bears at one end, ii) a substrate of the target enzyme and, at the other end, iii) a phenoxy derivative which, when it is released by said fragmentation, for giving the corresponding phenol derivative, belongs to the class of ESIPT fluorophores. In order to overcome the unfavorable sacrificial kinetics which are associated with an amino ethyl carbonate spacer which bears a primary amine group in a distal position relatively to the tertiary carbonate group, the present invention proposes a group of novel diamine spacers which are substituted in such a way that they are pre-organized for cyclization into a cyclic urea. This pre-organization accelerates the sacrificial process during the transformation with an enzyme. Further, the cyclization of the spacer used within the scope of the invention forms ureas which are known for their great stability and their general biocompatibility.

This technological innovation gives the possibility of obtaining two fundamental properties for the corresponding molecular probe: (a) it makes it insensitive to spontaneous degradation and therefore to the production of a falsely positive fluorescent signal, and (b) it gives rapid fragmentation kinetics during the transformation by the target enzyme for a performance suitable for applications in the field of life sciences. The group $R_0$ is capable of being cleaved from the remainder of the substrate by action of the target peptidase, which leads to an intermediate which is spontaneously and rapidly sacrificed for producing a fluorescent signal.

The precipitate which may be obtained from the peptidase substrate by cleavage of the covalent bond between NH and $R_0$, followed by cleavage of the —C(O)—$R_5$ bond following cyclization of the spacer, gives a fluorescent signal. According to a particular embodiment, this precipitate is strongly fluorescent while the original peptidase substrate is not very fluorescent or not at all fluorescent; the impact probe thus operates according to the OFF/ON mode.

According to another aspect, the invention relates to a method for detecting the presence of a catalytically active peptidase, by means of a substrate according to the invention. More specifically, the invention relates to a method for detecting the presence of a catalytically active peptidase comprising the steps of:
  contacting a sample suspected of containing said peptidase with a substrate according to the invention;
  applying suitable conditions for allowing the formation of a fluorescent precipitate; and
  quantivately or qualitatively analyzing said fluorescent precipitate.

In particular, such a detection method may be applied under physiological conditions, relatively in an aqueous medium buffered to a pH of the order of 7.4.

In an embodiment of the invention, the analysis of the fluorescent precipitate comprises the following steps:
  exposing the fluorescent precipitate to a light source capable of producing light with an absorption wavelength of the fluorescent precipitate; and
  detecting the resulting fluorescence of the precipitate.

The invention will be described in more detail. First, certain terms used in the definition of the substrate (I) will be defined.

By "alkyl" is meant a saturated hydrocarbon chain which may be linear or branched. Methyl, ethyl, n-propyl, isopropyl, iso-butyl and tert-butyl are examples of ($C_1$-$C_4$)alkyl (alkyl with 1 to 4 carbon atoms) groups.

By "aryl" is meant a phenyl, naphthyl or cinnamyl group.

By a "peptidyl" group, is meant a sequence of at least two amino acids bound together through a peptide bond. Within the scope of the invention, the amino acid(s) present in $R_0$ may be either natural amino acids or not, but preferably will be selected from the 20 natural amino acids (=proteinogenic amino acids), optionally in a salified or protected form. The N-terminal function of the terminal amino acid may optionally be salified or functionalized. As an example of a salified form, mention may be made of the hydrochloride, tosylate or trifluoroacetate form.

By "side chain of an amino acid", is meant the side chain of primary amino acids. As an example of such a side chain, mention may be made of methyl (side chain of alanine), iso-propyl (side chain of valine), iso-butyl (side chain of leucine), benzyl (side chain of phenylalanine) groups.

"Fluorescence" is the property by which a molecule which is excited with light of a given wavelength emits light at a greater wavelength. Fluorescence is a phenomenon which results from the interaction of a fluorophore with an incident photon. This process is called excitation. The absorption of the photon causes an electron in the fluorophore to pass from its fundamental state to a higher energy level. Subsequently, the electron returns to its original level by emitting a photon. This process is called fluorescence emission. The fluorophore then emits light at a greater wavelength than that of the absorbed photon. This is simply due to the fact that the energy of the emitted proton is less than that of the absorbed photon, because of the energy dissipation during the lifetime of the excited state. This definition is given in patent application WO 2004/058787.

The compounds (I) according to the invention are called "peptidase substrate" since they are transformed into another substance during a chemical reaction catalyzed by a peptidase. During such a reaction, the compounds (I) (also called "probe") are cleaved into a fluorescent precipitate and a non-fluorescent product by the action of the specific peptidase.

$R_5$ comprises an O-phenyl group in which the phenyl group is substituted and/or condensed with one or several unsaturated carbocycles optionally comprising a heteroatom such as nitrogen. This phenoxy derivative, symbolized by —O-Ph, when it is not bound to the substrate corresponds to a phenolic derivative HO-Ph which belongs to the class of the ESIPT fluorophores. $R_5$ corresponds to such a fluorophore HO-Ph bound to the substrate through an oxo bridge, according to the sequence —CO—O-Ph.

The phenoxy derivative $R_5$ symbolized by —O-Ph which, if it is not bound to the substrate, corresponds to an ESIPT fluorophore, made for example correspond to the following preferred structures (A) or (B):

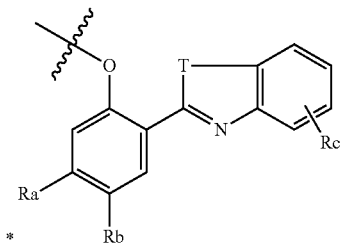

(A)

wherein:
T is —NH—C(O)—, —S—, —O—, —NH, N-alkyl or N-aryl,
Ra is hydrogen or an electron attractor carbonaceous substituent, such as —CN or —COORd, with Rd which represents a ($C_1$-$C_4$)alkyl group, or else $R^a$ is —CONReRf, with Re and Rf, either identical or different, which represent hydrogen or a ($C_1$-$C_4$)alkyl group, or else Ra is —$CF_3$, or a 2-oxazolyl, 2-thiazolyl, 2-imidazolyl (either benzo-condensed or not), 4-pyrimidinon-2-yl, or quinazolinon-2-yl group,
Rb is hydrogen, a chlorine atom, —OH, —$NH_2$, —NRgRh or —ORg, with Rg and Rh, either identical or different, which represent a ($C_1$-$C_4$)alkyl,
or else Ra and Rb are bound together so as to form a hydrocarbon chain comprising 4 or 5 members, either saturated or unsaturated, substituted or non-substituted, optionally interrupted by one or several heteroatoms selected from N, S and O,
Rc is hydrogen, Br, Cl, I or F,

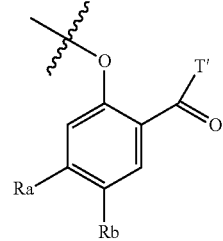

(B)

wherein:
T' is $NH_2$, OH, an aryl group, a ($C_1$-$C_4$)alkyl group, SH, NHR, OR, NRR', SR, with R and R' which represent a ($C_1$-$C_4$)alkyl or an aryl,
Ra is hydrogen or an electron attractor carbonaceous substituent like —CN, or —COORd, with Rd which represents a ($C_1$-$C_4$)alkyl group, or Ra is —CONReRf, with Re and Rf, either identical or different, which represent a hydrogen or a ($C_1$-$C_4$)alkyl group, or else Ra is —$CF_3$, or a 2-oxazolyl, 2-thiazolyl, 2-imidazolyl (benzo-condensed or not), 4-pyrimidinon-2-yl, or quinazolinon-2-yl),
Rb is hydrogen, a chlorine atom, —OH, —$NH_2$, —NRgRh or —ORg, with Rg and Rh, either identical or different, which represent a ($C_1$-$C_4$)alkyl group,
or else Ra and Rb are bound together so as to form a hydrocarbon chain comprising 4 or 5 members, either saturated or unsaturated, substituted or non-substituted, optionally interrupted by one or several heteroatoms selected from N, S and O.

When the target peptidase has released a free primary amino group at the end opposite to the carbamyl group of the spacer, the latter cyclizes spontaneously thereby releasing the phenol which thus becomes strongly fluorescent.

In a particular embodiment, the peptidase substrate according to the invention is of formula (IA):

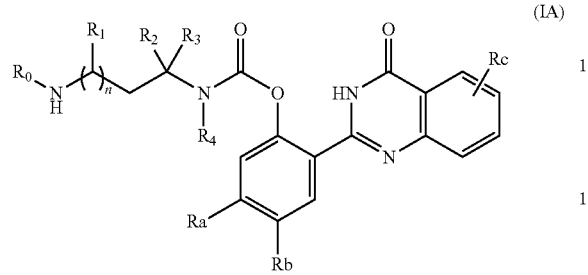

(IA)

wherein n, $R_0$, $R_1$, $R_2$, $R_3$, $R_4$, Ra, Rb and Rc are defined as above for (I) and (A). According to particular embodiments, the invention relates to compounds of formula (I) with $R_5$ which represents a group (A) or (B) and to compounds of formula (IA), Ra=Rb=Rc=H or else Ra=H, Rb=Rc=Cl with Rc, preferably in the para position relatively to the position of the nitrogen atom. According to other particular embodiments, Ra and Rb are bound together, so that the substrate according to the invention fits the formula (IA') or (IB'):

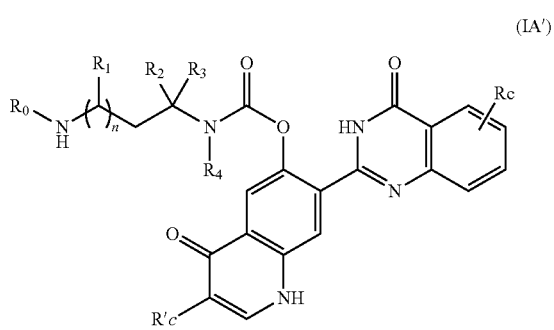

(IA')

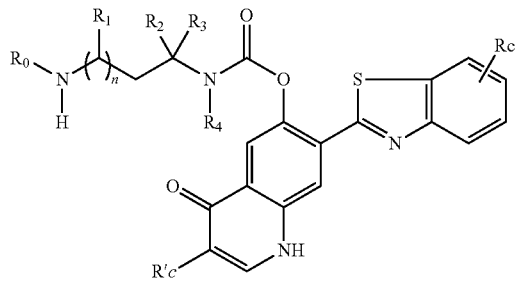

(IB')

wherein n, $R_0$, $R_1$, $R_2$, $R_3$, $R_4$ and Rc are defined as above for (I) and (A) and R'c represents a hydrogen atom or a —COO($C_1$-$C_4$)alkyl group. The compounds in which Rc=H or Cl in a para position relatively to the nitrogen atom are preferred.

In an embodiment of the substrates (I), (IA), (IA') and (IB') according to the invention, $R_2$=H and $R_3$ and $R_4$ are bound together and form a sequence —$(CH_2)_m$— with m=3, 4 or 5.

In another embodiment of the substrates (I), (IA), (IA') and (IB') according to the invention, $R_2$, $R_3$ and $R_4$, either identical or different, are a ($C_1$-$C_4$)alkyl, for example a methyl or an ethyl, for example $R_2$=$R_3$=$R_4$=—$CH_3$.

Both of these kinds of way for pre-organizing the ethylene diamine spacer, for cyclization into a cyclic urea, either consisting of introducing two alkyl substituents on the alpha carbon of the carbamate group or of including the bond between the nitrogen of the carbamate group and its alpha carbon in a heterocycle, accelerate the sacrificial process. The bond between the nitrogen of the carbamate group and its alpha carbon is for example introduced into a heterocycle belonging to the class of pyrrolidines (with 5 members) or to that of piperidines (with 6 members).

In these different embodiments, n may be equal to 0 or to 1. In the case when n=1, $R_1$ will preferably be a methyl, iso-propyl, iso-butyl or benzyl group.

The Scheme 4 hereafter shows two examples of fluorogenic substrates (Examples I.1 and I.2) and the cascades of reactions according to which they fragment, after initiation due to the cleavage by the target peptidase in the case when n=0.

Scheme 4

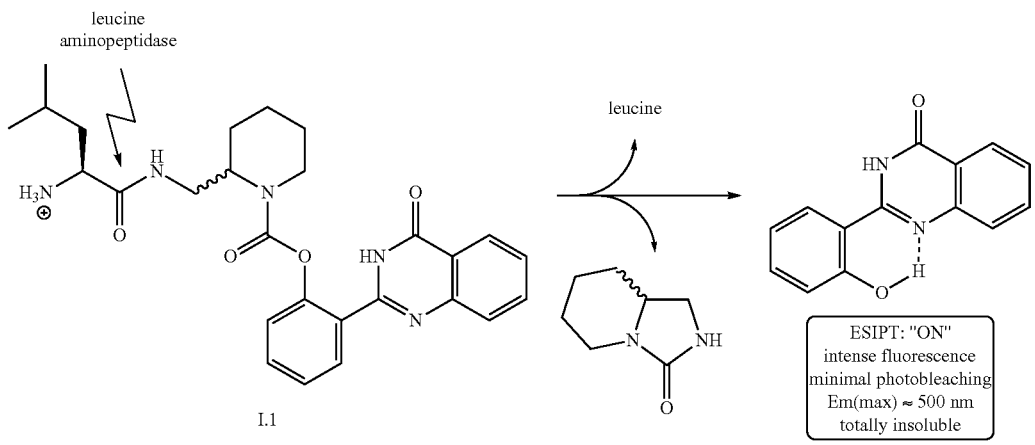

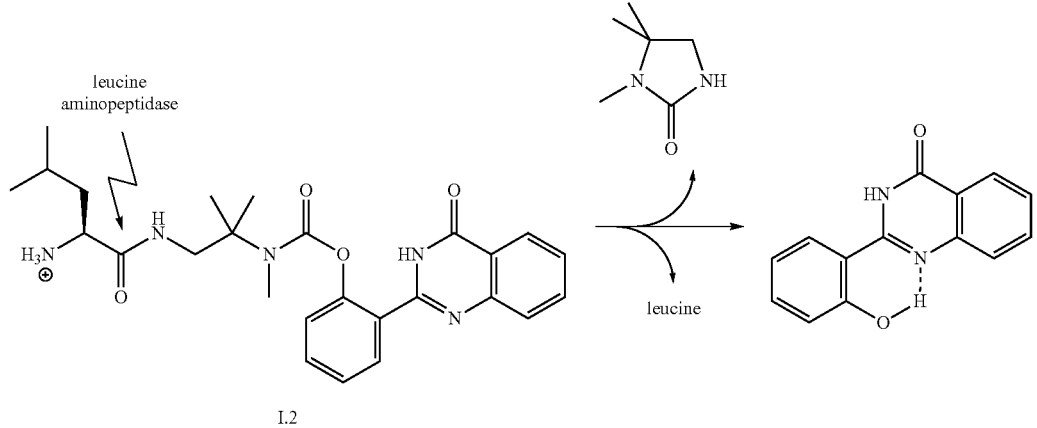

The following substrates I.3, I.4 and I.5 represent three other examples according to the invention wherein n=0.

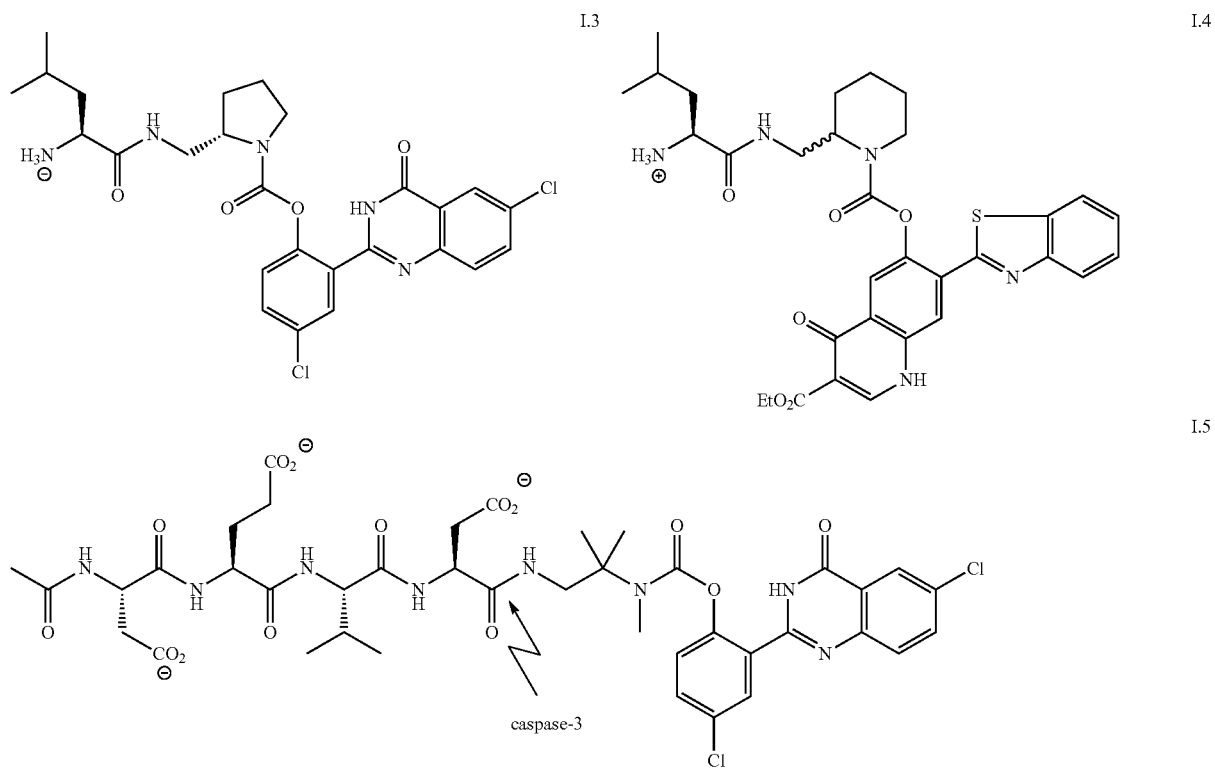

It is also possible that n=1. In this case, $R_1$ will preferably be different from hydrogen and may for example represent a methyl group. The substrate I.6 hereafter represents an example according to the invention in which the spacer group with n=1 mimics the side member of the first amino acid residue beside the C-terminal of the scissile peptide bond (the position "P1'" according to the convention of Schechter and Berger; Schechter and Berger (1967) Biochem. Biophys. Res. Commun. 27 (2): 157-162). The benefit of working with a spacer in which n=1 according to the invention consists in the increase in the molecular recognition by an endoprotease (such as PSA) for the probe which also has the 1st "post-scissile" side member (a methyl for alanine) of the preferred peptide sequence of the target peptidase, (Coombs et al. Chem. Biol. 1998, 5, 475), this in order to increase the conversion rate, or even to observe any transformation for certain endoproteases. It should be emphasized that the presence of this member should provide a kinetic advantage to the sacrifice of the spacer, which may give the possibility of at least partly compensating for the rate loss due to the passage from a spacer with five members (n=0), to a spacer with six members (n=1). Further, the substrate I.6 comprises a dichloro derivative of the HPQ used by Invitrogen-Molecular Probes for its ELF 97 technology for the advantageous granularity of its precipitate in the physiological medium.

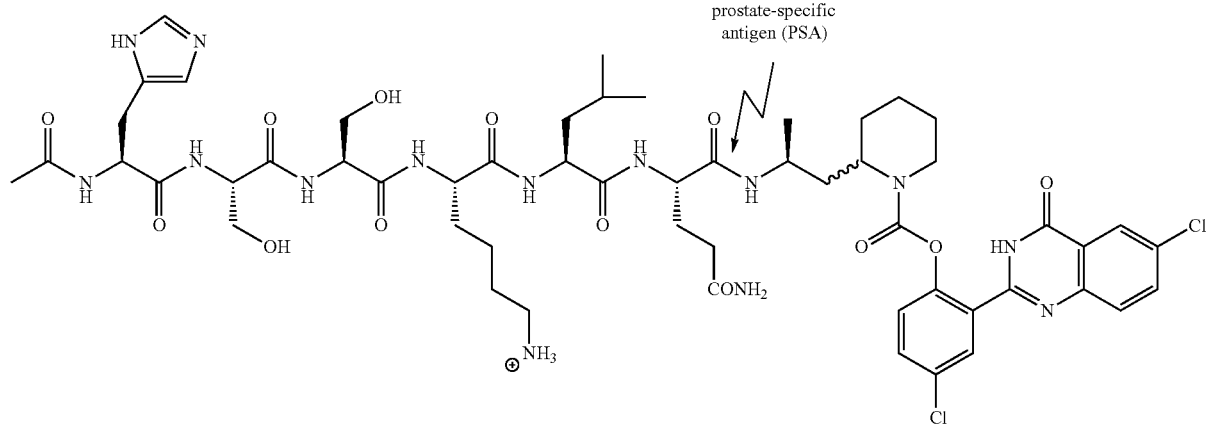

= Ac-HSSKLQ-spacer-dichloroHPQ

Examples I.1 and I.2 comprise the conventional ESIPT fluorophore hydroxyphenyl-quinazolinone ("HPQ") (U.S. Pat. No. 3,169,129), and Examples I.3, I.5 and I.6, dichloro-HPQ, for which the maximum emission wavelength is located between 500 and 550 nm according to the substitution pattern. However, this invention is applicable to all the phenols with which it is possible to obtain an ESIPT phenomenon, as this is the case of Example I.4 since the chemistry for suppressing ESIPT fluorescence is identical and simple: the incorporation of the phenolic hydroxyl into the carbamate group prevents the formation of the internal hydrogen bond. In the invention, the most simple fluorophore (A) with Ra=Rb=H may be used. A more complex fluorophore with various substitutions may be used. For their preparation, reference may be made to EP 0641 351 or WO 2004/058787, for example.

Certain examples of ESIPT phenolic fluorophores which may be used within the scope of the invention and which are described in the literature, their excitation and emission maxima, as well as their quantum yield ("QY") are listed hereafter.

1

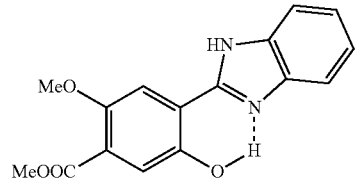

fluorescence (MeCN)
370 (Exc)/570 (Em)
QY: 0.20

2

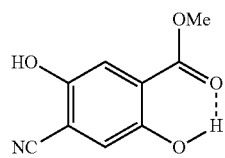

"bright blue fluorescence"
(H$_2$O) 360 (Exc)/516 (Em)
QY: 0.60

-continued

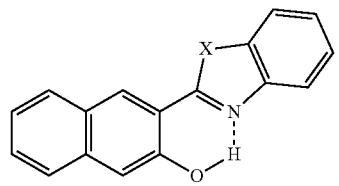

3a X = O, no brightness, no QY published
Exc: 360; Em(max): 670 nm
3b X = NH, 300/600

4

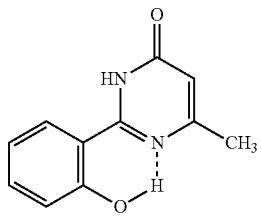

"intense green fluorescence"

5

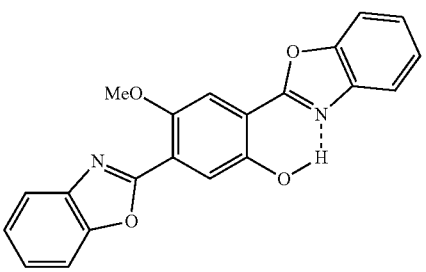

in 3-methyl-pentane: Exc (max): 385 nm
Em (max): 550 nm
QY = 0.50

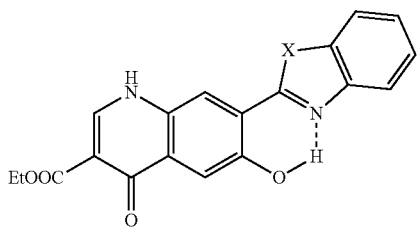

X = O Ex/Em 429/596 nm QY: 0.15
X = S Ex/Em 442/636 nm QY: 0.25

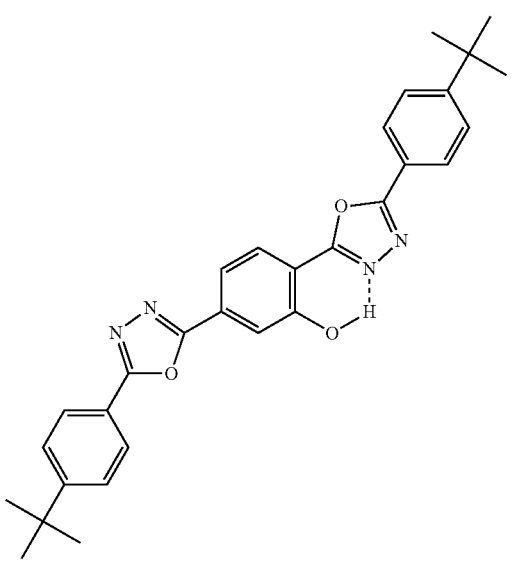

solid state (QY = 0.47). in solution
(QY = 0.40, CHCl3). (EM = 486 nm).

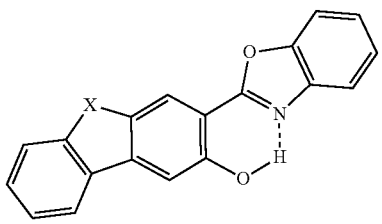

(excited at 350 nm in toluene)
X = O Em(max): 545 nm QY 0.40
X = S Em(max): 565 nm QY 0.36
X = NEt Em(max): 600 nm QY 0.21

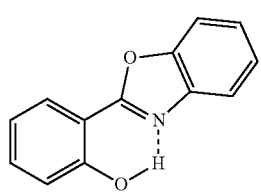

(excited at 300 nm in the solid state)
X = S 517 nm (Em) QY 0.30
X = O 506 nm (Em) QY 0.42
X = NH 462 nm (Em) QY 0.035

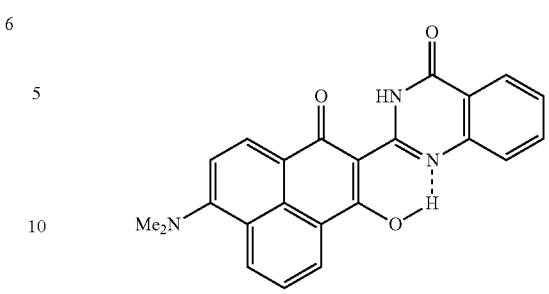

1: Stefani, V., et al. Dyes and Pigments (1992)20, 97-107.
2: Yamada, S., et al. Chemistry Letters (1999), 197-198.
3a: Nagaoka, S., et al. Journal of Photochemistry and Photobiology a-Chemistry (1999)122, 151-159.
3b: Douhal, A., et al. Chemical Physics Letters (1994)217, 619-625.
4: Kemp, D. S., et al., Journal of Organic Chemistry (1981)46, 1804-1807.
5: Mordzinski, A., et al. Journal of Physical Chemistry (1986)90, 1455-1458.
6: Lins, g.O.W., et al. Dyes and Pigments (2010)84, 114-120.
7: Seo, J., et al. Journal of Photochemistry and Photobiology a-Chemistry (2007)191, 51-58.
8: Kauffman, J. M., et al. Journal of Heterocyclic Chemistry (1995)32, 1541-1555.
9: Heller, A., et al. J. Phys. Chem. (1970)74, 4473-4480.
10: JP2004142131.

Thus, the group $R_5$ may be selected so that the peptidase substrate releases a fluorophore Ph-OH selected from the ESIPT phenolic fluorophores 1, 2, 3a, 3b, 4, 5, 6, 7, 8, 9 and 10, after cleavage by the target peptidase.

All the possible peptidyl or amino acid groups making up the substrates of peptidases may be used in $R_0$ present in the compounds of formulae (I), (IA) or (IA'). The amino acids may be either functionalized or not, in particular on the N-terminal end of $R_0$. According to an embodiment of the invention, the peptidyl residue has at most 10 amino acids which may be identical or different. According to a particular embodiment, for reasons of costs of the substrate, the peptidyl residue has at most six amino acids either identical or different. The amino acids of the peptidyl residue are preferably selected from natural amino acids. Nevertheless, the N-terminal end of the amino acid or of the peptidyl group may be functionalized with an acyl group —COR", R" being a $(C_1-C_6)$alkyl group or a O—$(C_1-C_6)$alkyl group. The possible functionalization of the N-terminal end of a given probe with an acyl group R"CO—) stems from the fact that certain endoproteases will not interact with the substrate having a free amino group at its end. Also, this N-terminal functionalization will be preferred in the case when $R_0$ represents a peptidyl group, while in the case when $R_0$ represents an amino acid, its N-terminal function will be free, or preferably salified in the form of ammonium. The solid phase peptide synthesis (SPPS) by means of carbonate protective groups (which also form "acyl" groups in this context) often allows a more simple synthesis of a probe having a carbonate at this N-terminal end. In the case of amino peptidases, the use of a group $R_0$ which represents an amino acid, is preferably used, while in the case of endopeptidases, the use of a group $R_0$ which represents a peptidyl group will be preferred. The embodiments with n=1 and $R_1$ which represents a side chain of amino acid such as a methyl, iso-propyl, iso-butyl or benzyl group are particularly advantageous in the case when $R_0$ is a peptidyl group and not a single amino acid.

As examples, the following peptidyl groups may be mentioned: Leu (for leucine aminopeptidase), Ser-Gln-Asn-Tyr (the N-terminal portion of the preferred cleavage sequence of the peptidase of HIV-1), Asp-Glu-Val-Asp- (for caspase 3), His-Ser-Ser-Lys-Leu-Gln (for the antigen specific to prostate "PSA") or the N-terminal end may be free or substituted with an acyl group "—COR", R" being a $(C_1-C_6)$alkyl group or an $O—(C_1-C_6)$alkyl group (for example a —COMe group).

The peptidyl or amino acid group is selected for its suitability with the known sequence selectivity of the targeted peptidase, which will recognize it. The peptidyl or amino acid group may be selected for the preferred action which a peptidase involved in certain diseases will have on the latter, as notably shown in Table 1.

TABLE 1

Examples of peptidases which may be used as biomarkers for biological phenomena or diseases during imaging.

| Peptidase | Class | Function | Disease |
|---|---|---|---|
| Leucine aminopeptidase | Zinc | Post-proteasomal ripening of peptides shown to be of class I | — |
| Caspase-3 | Cys | Apoptosis | Cancer |
| HIV-1 Peptidase | Asp | HIV replication | AIDS |
| Renin | Asp | Production of angiotensin I | Hypertension |
| Thrombin | Ser | Blood coagulation | Myocardial infarction |
| Tryptase | Ser | Phagocytosis | Asthma |
| Cathepsin K | Cys | Bone resorption | Osteoporosis |
| ACE | Zinc | Production of angiotensin II | Hypertension |
| Plasmepsin I and II | Asp | Degradation of hemoglobin | Malaria |
| β-Secretase | Asp | Synthesis of β amyloid | Alzheimer's disease |
| PSA (kallikrein III) | Ser | Liquefaction of sperm ejaculate | Prostate cancer |

Examples I.1 to I.6 target members of two different classes of peptidases: an exopeptidase, more specifically an aminopeptidase (leucine aminopeptidase EC 3.4.11.1 for I.1 to I.4) and two endopeptidases (a) caspase-3, EC 3.4.22.56 for I.5; (b) PSA=<<kallikrein III>>, EC 3.4.21.35 for I.6). While exopeptidases only cleave one amino acid residue from the end of a peptide chain, endopeptidases are, for the major part, true proteases which cleave a peptide bond inside a peptide backbone; they therefore have a greater or lesser specificity of sequences. The preferred sequence of cleavage of caspase-3 is: Asp-Glu-Val-Asp-Gly-Asp-. For creating fluorogenic probes, it is sufficient to provide the peptidase only with the N-terminal portion (on the left of the scissile peptide bond) of the preferred sequence, i.e. Asp-Glu-Val-Asp- (or in the one-word code: DEVD), although this is associated with a gradual loss of the catalytic transformation level. However, in order that caspase recognizes DEVD, the N-terminal end should be acetylated: a free amino-terminal would annihilate recognition by the enzyme.

The substrates (I) according to invention may be obtained by coupling of an amine of formula (II):

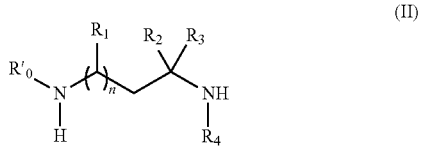

(II)

wherein $R_1$, $R_2$, $R_3$ and $R_4$ are as defined for the substrates of formula (I) and $R'_0$ represents a group $R_0$ which is as defined for the substrates of formula (I) or most often as such a group $R_0$ wherein the present amine or acid function(s) are protected with a chlorinated derivative of formula (III):

(III)

wherein $R_5$ is as defined for the substrates of formula (I), optionally followed by deprotection of the amine or acid functions of the substituent $R'_0$ in order to obtain $R_0$.

Such a coupling may notably be achieved in the presence of a base such as triethylamine.

The protection and deprotection reactions are carried out according to techniques well-known to one skilled in the art. The protection of the amine and acid functions will be effected by a temporary group for protecting amines, or carboxylic acids, well-known to one skilled in the art, such as those described in Protective Groups in Organic Synthesis, Greene T. W. and Wuts P. G. M., ed. John Wiley & Sons, 2006 and in Protecting groups, Kocienski P. J., 1994, Georg Thieme Verlag.

As an example of a group protecting amines and notably the amine present at the end of the chain of the amino acid or of the peptidyl residue, mention may be made of the tert-butoxycarbonyl (Boc) group and as an example of a group protecting acid functions, mention may be made of the tert-butyl group which leads to the intermediate formation of an ester.

Certain syntheses of compounds (II) are described in a detailed way in the examples which will follow and one skilled in the art may proceed by analogy. For preparation of the compounds (III), the latter may be obtained from the corresponding phenols already described in the literature, or even commercial phenols, for example, by the action of triphosgen.

The different compounds according to the invention may be found in all the possible forms of optical isomers or diastereoisomers, optionally in a mixture according to any proportions, unless specified otherwise. According to a particular embodiment, the compounds according to the invention including an asymmetric carbon are found in a racemic form, the forms R and S being found in substantially equal proportions. According to another embodiment, the compounds of formula (I) of the invention may be found in a form enriched in a diastereoisomer or enantiomer, with a diastereoisomeric excess or enantiomeric excess of more than 80% or even more than 95%, or even in a pure isomeric form i.e. with a diastereoisomeric or enantiomeric excess of more than 99%.

The compounds (I) are isolated in a form enriched in a diastereoisomer or enantiomer by conventional separation techniques: for example fractionated recrystallization of a salt of the racemic may be used with an optically active acid or base, the principle of which is well-known or most often conventional chromatographic techniques on a chiral or non-chiral phase.

The present invention makes the activity of the peptidases accessible through fluorescent imaging by using ESIPT fluorophores, for example, of the HPQ type (or of an HPQ analogue). No false positive signal due to spontaneous degradation (i.e. in the absence of a target peptidase, in a physiological medium) is observed. The probe itself is not very fluorescent or not at all (no intrinsic fluorescence), in particular at the emission wavelength of the free ESIPT fluorophore on which the detection/imaging instrument is adjusted. The probe thus operates in the off/on mode and may be used for developing analysis with maximum sensitivity. This invention gives the possibility of targeting exo-(amino-)peptidases but also endopeptidases with high selectivity for particular sequences of amino acids. This is possible by coupling of a specific peptide sequence of a particular endoprotease at the end of the smart spacer.

Further, the present invention represents an improvement as compared with that contained in Zhang, X.-B., Waibel, M., and Hasserodt, Chem. Eur. 1 (2010), 16, 792-795, in that the present probe is characterized by total absence of spontaneous degradation under physiological conditions and therefore does not lead to any slightest production of a false positive fluorescent signal. It overcomes the technological obstacle of slow sacrifice of the diamine spacers, if the nitrogen atom bearing $R_0$ bears a hydrogen rather than an alkyl group which is required for targeting peptidases which, with very few exceptions (prolidases) only cleave secondary peptide bonds and not tertiary peptide bonds. The cyclization rate loss which results therefrom (a factor of ten, according to Saari, W. S., et at., supra) is compensated by the pre-organization of the diamine spacer for forming cyclic urea, the process which leads to the release of the ESIPT fluorophore. The enormous gain in cyclization rate which is obtained by pre-organizing the spacer has already been demonstrated by the applicant for two independent molecular systems: Waibel, M., Zhang, X.-B., and Hasserodt, J. Synthesis (2008) 318-324; and Zhang, X. B., Waibel M., and Hasserodt, J. Chemistry-a European Journal (2010) 16, 792-795. In the first article, the fragmentation under physiological conditions was instantaneous, in the second it was very fast. However, none of the two systems benefits from the presence of the tertiary carbonate bond to the phenol and had residual degradation under physiological conditions.

The substrates of the present invention benefit from good permeability towards the cell membrane as compared with other known substrates of fluorogenic enzymes and will be capable of easily entering the cells (to be compared with: Duhamel, S. et al. Journal of Microbiological Methods 75 (2008) 269-278), so that these substrates may be used for different applications in a large variety of cells. Further, the substrates according to the present invention are generally soluble but not very fluorescent in a form that is solubilized in water (intrinsic fluorescence), however, they emit a highly fluorescent signal in an aqueous solution containing the substrate and the corresponding peptidase. In the case of HPQ, this fluorescent signal is emitted in the solid state by the precipitate formed under the action of the peptidase since HPQ is highly insoluble in most solvents, but in particular in aqueous media. Other ESIPT fluorophores are not either particularly soluble in aqueous media, but most of them keep their capability of emitting fluorescence even if they precipitate. The suitable conditions for allowing the formation of a fluorescent precipitate during hydrolysis by a peptidase are purely aqueous media, such as a buffered medium or a physiological medium. An important point is that the precipitate is formed during hydrolysis by a peptidase without compromising the peptidase activity. Thus, their use for localization studies in biological samples or the detection of discrete bands in non-denaturating PAGE and in Western blot transfer is possible. More details relating to the conditions and to the detection techniques which may be used, are given in WO 2004/058787 and EP-0 641 351 which may be directly applied to the present invention.

The probes according to the invention are attractive for many high sensitivity applications in life sciences, and notably: (1) high yield screening of peptidase activity expressed by bacterial colonies on a gelose plate (analysis on colonies); (2) the in vitro detection of peptidases in biological liquids (hematology and others).; (3) the viewing of peptidase activity at a simple cell in flow cytometry; (4) detection of sub-cell peptidases in cultivated cells (confocal fluorescence microscopy); (5) histochemical detection of peptidases (at a tissue scale;) and finally (6) in vivo imaging of an entire animal. The probes according to the invention meet requirements of experts in the field of the creation of probes having greater robustness than those which are presently available (National Research Council of the U.S.A. (2006) Visualizing Chemistry: The Progress and Promise of Advanced Chemical Imaging, The National Academies Press). In particular, the fast growing field of in vivo molecular imaging is lacking in smart stealth probes which are sufficiently robust, and with limited molecular complexity so as to be manufactured with limited costs (Baker, M. (2010). Whole-animal imaging: The whole picture. Nature 463, 977-980).

Thus, the peptidase substrates according to the present invention have a large number of potential applications. The examples of such applications include:

(a) the design of analyses on bacterial colonies. The latter are presently conducted on a gelose plate (Petri dish) where up to 3,000 colonies may be distinguished without having to actively separate them in separate compartments like the wells contained in a multiple-well plate. It is thus possible to (1) design tests on clinical samples giving the possibility of identifying from a set of bacterial lines a pathogenic line of interest; (2) to conduct massive parallel tests of a bank of proteins of its own production expressed by a conventional bacterial host (often a commercial host). This collection of proteins may of course contain a particular protein of interest, for example a protease having selectivity for a specific sequence of amino acids, or a protease hydrolyzing a non-natural carboxamide bond. In the field of directed development of proteins in general or enzymes in particular, there exists a strong demand for efficient and sensitive analyses for screening very large numbers of protein variants easily exceeding $10^6$. The application of the probe according to the invention may be more easily contemplated by dissolution in the gelose solution before it is poured into the plate where it gels. As an alternative, substrates are incubated with the colonies by immersion of a filter before it is pressed on the colonies. The main advantage to which the probe according to invention contributes for such an analysis on colonies, is the on-site precipitation of the fluorophore; a dilution of the fluorescent signal by diffusion is therefore highly reduced, which allows longer incubation periods and therefore greater sensitivity for the analysis. The very large Stokes displacement of HPQ (approximately 140 nm) or of any HPQ analog should not remain poorly estimated; it also contributes to the excellent sensitivity and makes it easily distinguishable from the native fluorescence stemming from the biological sample.

(b) In vitro (histology) and in vivo imaging. Taking into account the very low solubility of free HPQ and of any HPQ analog, any release of the latter in a complex biological environment allows imaging by fluorescence with high spatial control. Imaging by fluorescence is a technique widely applied for distinguishing sub-cell structures. The localization of a specific peptidase activity at a high resolution may be possible by using a probe according to the invention.

On the contrary, passive fluorescent probes (those which are not transformed by an enzyme) are equipped with a specific ligand of a cell receptor in order to be bound on this receptor by non-covalent interactions; they are therefore not without any dilution effects on the signal. Above all, a receptor at best is equivalent to a fluorescent marker. The sensitivity of an analysis based on such probes is necessarily much lower than that of an active probe which benefits from the catalytic amplification of the signal.

The probes according to the invention may also be used for macroscopic imaging by fluorescence, i.e. at an entire organism. If the probe penetrates into the cell wall in order to attain the pepsidase activity of interest, the release of the free fluorophore excludes fast dilution of the signal by sharing with the extra cellular space. Generally, this allows prolonged incubation periods before imaging, which are particularly useful when the enzymatic activity is weakly expressed.

The peptidase substrates according to the invention may be prepared according to known techniques, detailed in the following examples. For example, an optionally protected peptidyl or amino acid group may be grafted on the spacer group. After a coupling step for introducing the fluorophore via its phenolic hydroxyl, the peptidyl or amino acid group may be deprotected. The thereby obtained complete probe may be purified, before use with conventional techniques.

The following examples illustrate the invention but have no limiting nature.

General

Chromatography on a column was carried out on 60-mesh silica gel (40-63 μm). The $^1$H and $^{13}$C NMR spectra were recorded at 200.13 MHz and 50.13 MHz, respectively, in deuterated chloroform, unless indicated otherwise. The chemical shifts (δ) are indicated in ppm and noted with reference to tetramethylsilane or according to the residual signals of the solvent; the abbreviations s=singulet, d=doublet, t=triplet, m=multiplet, br=broad are used. The NMR coupling constants (J) are indicated in Hertz. The analyses by fluorescence were carried out in black polypropylene 96-well (Corning, Corning Inc.) or 384-well (NUN-CLONE, Nunc Inc.) plates, and recorded on a fluorimeter with microplates (Mithras LB940 from Berthold Technologies). Except when this is specified, the chemicals were purchased with analytical reagent quality and used without any other purification.

Commercial dry THF and DCM were dried and purified by passing them over a column of activated alumina under argon (GT S100 Solvant Station System). The triethylamine was distilled from calcium hydride and retained on KOH tablets. The other reagents noted as dry reagents were dried on molecular sieves. Unless indicated otherwise, all the reactions were conducted in an air atmosphere with commercial solvents and reagents, without any additional drying or purification. Millipore water obtained from a purification system Elga Purelab was used in all the experiments.

The following abbreviations are used:
Me=methyl
Et=ethyl
cbz=carbobenzoxy
tBu=tertiary Butyl
Boc=tert-butoxycarbonyl
DCC=dicyclohexylcarbodiimide
TEA=triethylamine
pTsOH=para-toluene-sulfonic acid
EA=ethyl acetate
Cy=cyclohexane
HOBt=N-hydroxybenzotriazole
TFA=trifluoroacetic acid
THF=tetrahydrofurane
Leu=L-Leucyl
BocLeu=N-(tert-butoxycarbonyl)-L-leucyl
EDC=1-ethyl-3-(3,5-dimethylaminopropyl)-carbodiimide hydrochloride
TLC=thin layer chromatography
DMF=dimethylformamide
DCM=dichloromethane
DDQ=2,3-dichloro-5,6-dicyano-1,4-benzoquinone
DCU=di-cyclohexylurea
PLA=microsomal leucine aminopeptidase,

EXAMPLE I.1

The substrate I.1 is prepared as described in the following Scheme 5.

Scheme 5: chemical synthesis of Example I.1

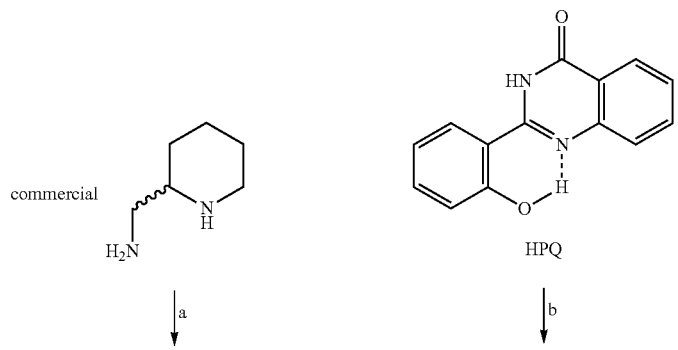

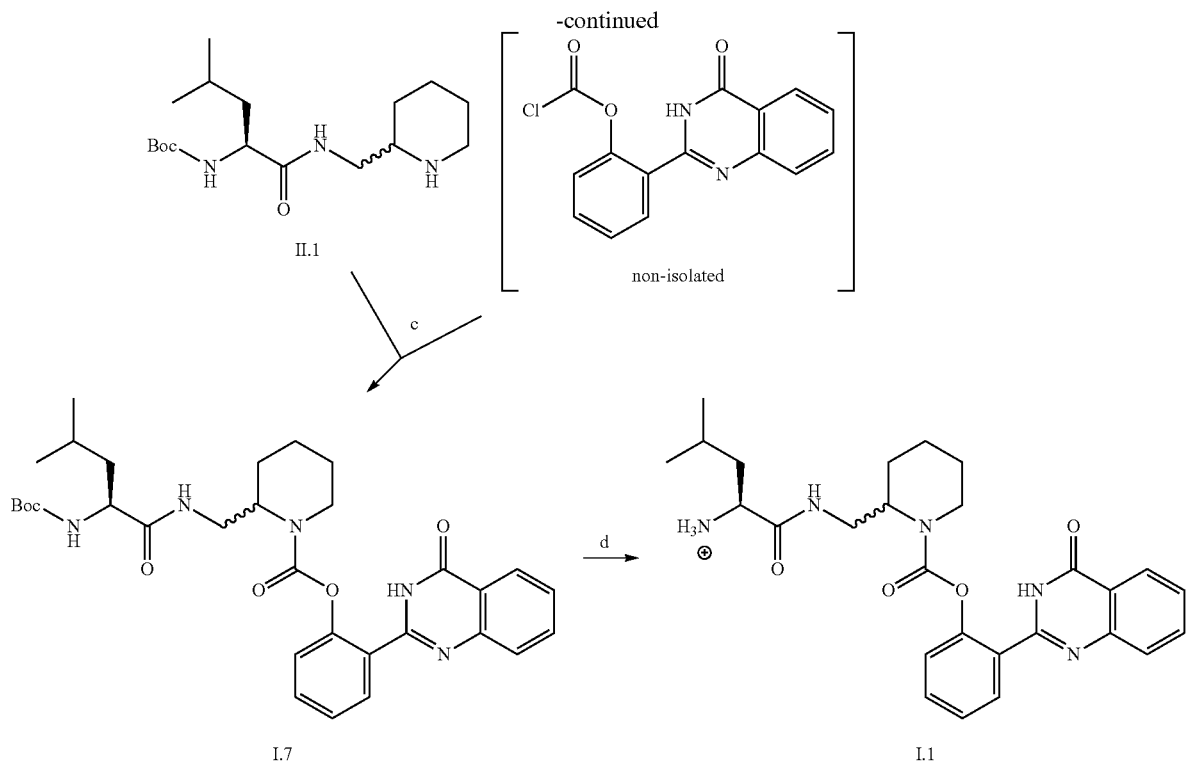

a) BocLeuOH, DCC; b) triphosgen; c) triethylamine; d) pTsOH.

Preparation of the Compound II.1: BocLeuOH (4385 g, 19.0 mmol; commercial; Fluka, 15450, ≥99.0%) is totally dissolved in dry DCM (50 mL) under an anhydrous atmosphere, before lowering the temperature of the mixture to 0° C. with an ice bath. Some DCC (3.95 g, 19.1 mmol) is added and the mixture stirred for 5 minutes before adding aminomethylpiperidine (2.11 g, 18.5 mmol; commercial; Aldrich 656518, 97%). The mixture is brought to room temperature by removing the ice bath. After 24 hours of stirring, the DCU having precipitated in the form of a white solid is removed by filtration on a frit with porosity 3 and the solid rinsed with DCM. The obtained yellow solution is washed with saturated $Na_2CO_3$ and then with 0.5 M phosphate buffer and at pH>10, then washed with brine, dried on $Na_2SO_4$ which is removed by filtration and evaporated in order to obtain a yellow oil (6.6 g). This oil is kept at 4° C. overnight, which causes precipitation of the DCU which is removed with the same procedure as described above. The NMR spectrum of the crude indicates the presence of the almost pure desired product, very slightly contaminated with a usual parasitic product of DCC couplings, i.e. DCU acylated by the amino acid. Purification on a silica column with an EA:Cy:MeOH gradient (1:1:0=>1:1:1, v:v:v) gives the product II.1 pure in the form of a colorless solid (2.703 g; 42%). The NMR spectra (a) show the presence of two diastereoisomers in a molar ratio 1:1 due to the presence of the stereogenic centre at the piperidine ring and (b) seem to be complicated by the presence of various conformational isomers of the ring.

$^1$H NMR (200 MHz, $CDCl_3$): 7.09-6.81 ((s, br+s, br), 1H), 5.70-5.34 ((s, br+d, br, 7.6 Hz), 1H), 4.08-3.98 (m, 1H), 3.31-3.15 (m, 1H), 3.11-2.90 (m, 2H), 2.70-2.44 (m, 2H), 2.14 (s, br, 1H, solvent and concentration sensitive shift, NH), 1.76-1.41 (m, 6H), 1.33 (s, 9H), 1.32-1.00 (m, 3H), 0.88 (d, 2.1 Hz, 3H), 0.87 (d. 2.4 Hz, 3H) ppm.

$^{13}$C NMR (125 MHz, $CDCl_3$): Diastereoisomer 1: 173.0; 155.7; 79.6; 55.8; 53.2; 46.5; 45.0; 41.3; 30.1; 28.3 (×3); 26.3; 24.7; 24.2; 22.9; 22.0; Diastereoisomer 2: 173.1; 155.8; 79.7; 55.5; 53.2; 46.5; 45.1; 41.2; 30.2; 28.3 (×3); 26.2; 24.7; 24.2; 22.9; 22.0 ppm. HSQC, COSY and jmod spectra complete the assignment of the signals.

HRMS (TOF MS ESI+) calculated for $[C_{17}H_{34}N_3O_3]^+$= $[MH]^+$: m/z=328.2595, found 328.2589.

Preparation of the Compound I.7: In a two-neck flask containing HPQ (76 mg; 0.32 mmol) in an anhydrous argon atmosphere, is added dry TEA (57 mg; 0.56 mmol; 1.8 equiv.) and dry DCM (1.2 mL) and the mixture is cooled to 0° C. Under stirring, a solution of triphosgen (124 mg; 0.42 mmol) in dry DCM (1.2 mL) is rapidly injected. The mixture is stirred at 0° C. for 40 minutes, and then for 20 minutes at 25° C., before being dry evaporated by means of a vane pump protected with two liquid nitrogen traps. The resulting beige solid is treated at room temperature with a solution of the compound II.1 (19 mg; 0.058 mmol; 0.2 equiv.) in dry TEA (101 mg; 1 mmol; 3 equiv.) and dry DCM (1.2 mL). The olive green colored solution is stirred for two hours before being poured on saturated $NaHCO_3$. The aqueous phase is extracted with $CHCl_3$, and the organic phases are collected and washed with saturated $NaHCO_3$ and with brine, and then dried with $Na_2SO_4$ which is removed by filtration, and dry evaporated. The residue is taken up in $CHCl_3$ and filtered twice on Celite in order to remove a portion of the remaining HPQ, and the filtrate is evaporated in order to obtain a solid greenish pasty solid (70 mg). Purification on a silica column (gradient EA:Cy:MeOH, 2:2:0=>2:2:1, v:v:v) leads to the pure compound I.7 (15 mg; 0.025 mmol; 44%). The NMR spectra (a) show the presence of two diastereoisomers in a molar ratio 1:1 due to the presence of the stereogenic centre at the piperidine ring and (b) seem to be complicated by the presence of various conformational isomers of the ring, which gives up to four resonances per single nucleus.

$^1$H NMR (500 MHz, CDCl$_3$): δ=8.60 (s, br; 0.5H); 8.36-7.92 (m, 2H); 7.89-7.78 (m; 2.5H); 7.58-7.47 (m; 2H); 7.39-7.35 (m; 1H); 7.31-7.15 (m; 1H); 6.86-6.81 (m; 0.1H); 5.66-5.60 (m; 0.1H); 5.05-4.88 (d, br+d, br; 8.5 & 6.5 Hz; 1H; NH$_{carbamate}$); 4.71-4.66 (m; 0.8H); 4.46-4.34 (m; 1H); 4.20-3.94 (m; 1H); 3.87-3.51 (m; 1H); 3.43-2.89 (m; 2H); 1.77-1.43 (m; 9H); 1.09-0.84 (m, 15H) ppm.

$^{13}$C NMR (125 MHz, CDCl$_3$): δ=174.6; 174.0; 171.3; 163.4; 162.9; 156.1; 155.7; 153.5; 152.8; 151.5; 151.2; 149.9; 149.7; 149.6; 149.4; 134.9; 134.9; 134.8; 132.1; 131.9; 130.7; 129.8; 128.3; 128.0; 127.1; 126.8; 126.6; 126.3; 126.1; 124.6; 123.1; 121.1; 120.9; 79.8; 54.4; 53.1; 52.6; 50.8; 43.6; 41.6; 41.3; 41.2; 39.9; 39.8; 39.7; 38.8; 29.4; 28.3; 28.2; 28.0; 27.1; 26.9; 25.6; 25.3; 24.9; 23.0; 22.3; 19.6; 19.3 ppm.

HRMS (TOF MS ESI$^+$) calculated for [C$_{32}$H$_{42}$N$_5$O$_6$]$^+$=[MH$^+$]: m/z 592.3130; found 592.3123.

Preparation of the Compound I.1: The compound I.7 (174 mg; 0.294 mmol) is dissolved in dry ethanol (10 mL) containing pTsOH.H$_2$O (61 mg, 0.32 mmol), put under an argon atmosphere and heated to 80° C. for 8 hours. The reaction is followed by TLC (EA:Cy:MeOH 1:1:1, v:v:v; UV and ninhydrin). HPQ trace amounts may appear. The crude solution is subject to purification on a silica column and trace amounts of HPQ are successively obtained (EA:Cy:MeOH 1:1:0, v:v:v), as well as residual trace amounts of I.7 (EA:Cy:MeOH 1:1:0.15, v:v:v), and the crude product I.1 (EA:Cy:MeOH 1:1:0.3, v:v:v) in the form of a solid (149 mg) which emits slightly blue fluorescence under a UV lamp. Its trituration with water removes possible excess of TsOH and the remaining solid (107 mg) gives a $^1$H NMR spectrum which indicates a molar ratio of 1:1 I.1:tosylate.

This solid is not very soluble in water but may easily be dissolved in MeOH (0.6 mL) before being diluted with water without any fear of precipitation. The NMR spectra (a) show the presence of two diastereoisomers in a molar ratio 1:1 due to the presence of the stereogenic centre at the piperidine ring and (b) seem to be complicated by the presence of various conformation isomers of this ring, which gives up to four resonances per single nucleus.

$^1$H NMR (D$_2$O, 500 MHz): δ=8.20 (d; 8.1 Hz; 1H); 7.94 (t apparent; 7.9 Hz; 1H); 7.77-7.70 (m; 3H); 7.68-7.65 (m; 1H); 7.51-7.47 (m; 1H); 7.36-7.32 (m; 1H); 4.52-2.77 (m; 6H); 1.65-1.22 (m; 9H); 0.81-0.70 (m; 6H) ppm.

$^{13}$C-NMR (D$_2$O, 125 MHz): δ=170.5; 170.3; 162.3; 162.2; 154.1; 153.9; 153.8; 148.2; 148.1; 141.7; 141.3; 137.1; 137.1; 135.1; 134.8; 130.2; 130.2; 129.6; 127.0; 123.6; 123.4; 123.3; 122.4; 122.3; 122.1; 122.0; 119.2; 52.0; 51.9; 51.6; 51.4; 50.9; 40.5; 40.0; 40.0; 39.9; 38.2; 25.8; 25.0; 25.0; 24.5; 23.9; 23.9; 21.8; 20.9; 20.8; 18.2; 18.0 ppm.

MS (ESI, positive mode): m/z 492.3: [MH]$^+$. MS (ESI, negative mode): m/z 490.2: [M-H]$^-$.

The analysis by HRMS (TOF MS ESI$^+$) on the cation was performed on a sample having the same NMR spectra but prepared by substantially applying the same procedure used for the preparation of compound I.2 (the compound I.7 is then used instead of the compound I.8); including, calculated for [C$_{27}$H$_{34}$N$_5$O$_4$]$^+$=[MH$^+$]: m/z 492.2605, found 492.2592.

EXAMPLE I.2

The substrate I.2 is synthesized as described above for the substrate I.1 except that instead of aminomethyl-piperidine (commercial compound), first of all N$^2$-2-dimethylpropane-1,2-diamine (13) must be synthesized in three steps according to suitable procedures of the literature.

Scheme 6: chemical synthesis of Example I.2

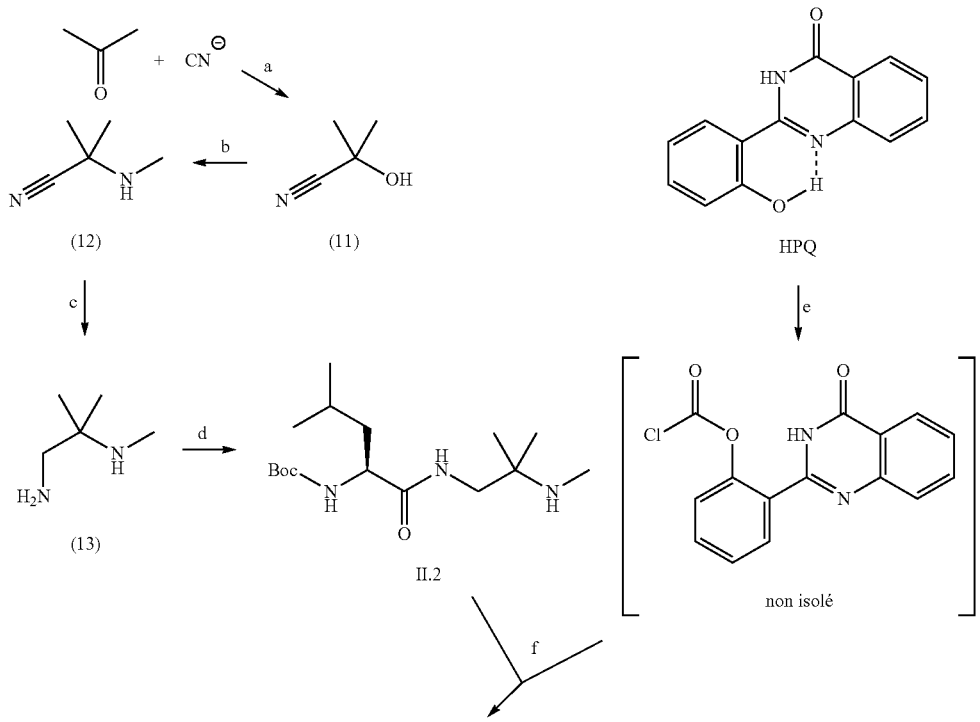

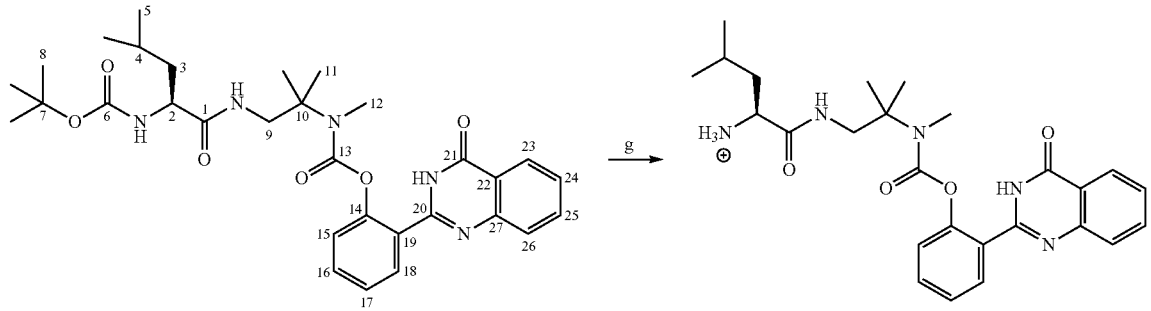

a) Na₂S₂O₅, H₂O; b) CH₃NH₂; c) LiAlH₄; d) BocLeuOH, DCC; e) triphosgen; f) TEA; g) TFA.

Preparation of the Compound (11): (acetone cyanohydrine; adapted from Faghihi, K.; Zamani, K.; Mirsamie, A.; RezaSangi, M., *Eur. Polym. J.* 2003, 39 (2), 247-254.) A gently stirred aqueous solution (20 mL) of sodium metabisulfite (11 g, 58 mmol) is treated with acetone (5.8 g, 100 mmol). Addition of an aqueous solution (20 mL) of potassium cyanide (6 g, 92 mmol) causes separation of the desired acetone cyanohydrin into a second phase (upper phase). Once this reaction is completed, both phases are separated and the upper one is dried on Na₂SO₄ and filtered in order to obtain pure acetone cyanohydrin (11) in the form of a clear liquid (5.402 g, 69%). $^1$H NMR (200 MHz, CDCl₃): δ=1.43 (s, 6H, 2×CH₃) ppm; $^{13}$C-NMR (50 MHz, CDCl₃): δ=29.4 (2×CH₃), 65.3 ($\underline{C}$(Me)₂), 123.0 (C≡N) ppm; MS (ESI, positive mode): m/z 86.1: [MH]⁺.

Preparation of the Compound (12): (2-methylamino-2-methyl-propionitrile; adapted from Exner, L. J.; Luskin, L. S.; de Benneville, P. L., *J. Am. Chem. Soc.* 1953, 75(19), 4841-4842.) An aqueous solution (40% by a mass) of methylamine (2.8 g, 36 mmol) is slowly added to acetone cyanohydrin (11) (1 g, 12 mmol) located in a flask placed in ice bath. The addition is carried out slowly so that the temperature of the mixture does not exceed 15° C. Once the addition is completed, the reaction mixture is stirred for one hour and a half. The obtained solution is extracted with Et₂O (3×10 mL). The organic phases are combined and dried on Na₂SO₄ which is then removed by filtration. The solvent is removed under reduced pressure in order to lead to the product (12) in the form of a colorless liquid (0.700 g, 59%). $^1$H NMR (200 MHz, CDCl₃): δ=1.21 (s, 6H, 2×CH₃), 2.27 (s, 3H, NCH₃) ppm; $^{13}$C NMR (50 MHz, CDCl₃): δ=27.5 (2×CH₃), 31.8 (NCH₃), 52.5 ($\underline{C}$(Me)₂), 122.8 (C≡N) ppm; MS (ESI, positive mode): m/z 99.1 [MH]⁺.

Preparation of the Compound (13): (N²-2-dimethylpropane-1,2-diamine; adapted from US 2005/0038078). 2-methylamino-2-methyl-propionitrile (12) (1.960 g, 20 mmol) is added dropwise to a suspension of lithium aluminium hydride (1.520 g, 40 mmol) in Et₂O (2 mL) in an argon atmosphere. The mixture is stirred for 3 hours at room temperature, and is then diluted in Et₂O (30 mL). Once it is placed in an ice bath, a saturated aqueous solution of K₂CO₃ is added until no more hydrogen evolvement is observed. Anhydrous Na₂SO₄ is then added to the reaction mixture which is stirred for 10 mins. The removal of the salts is carried out by filtration on Celite which is then washed with large volumes of Et₂O. The obtained filtrate is then concentrated under reduced pressure in order to obtain N²-2-dimethylpropane-1,2-diamine (13) in the form of a clear liquid (2.001 g, 98%). $^1$H NMR (200 MHz, CDCl₃): δ=2.40 (s, 2H), 2.14 (s, ~3H, NHMe), 1.8 (s, br, 3H, NH+NH₂), 0.87 (s, 6H, 2×Me) ppm; $^{13}$C NMR (50 MHz, CDCl₃): δ=53.0 (CMe₂), 50.2 (CH₂), 28.3 (NHMe), 23.0 (2×Me) ppm; MS (ESI, positive mode): m/z 103.1: [MH]⁺.

Preparation of Compound II.2: A solution of BocLeuOH (1.37 g; 5.92 mmol) in dry DCM (50 mL) at −5° C. is treated with DCC (1.227 g; 1 equiv.) and stirred for 5 minutes. N²-2-dimethylpropane-1,2-diamine (13) (1.50 g of a 47% by mass solution in Et₂O; >1 equiv.) is added before raising the temperature of the mixture to room temperature and leaving the mixture with stirring for 48 hours. The precipitated DCU (colorless) is filtered on a glass frit of porosity 3. The almost colorless filtrate is washed with saturated Na₂CO₃, in order to remove the residual BocLeuOH. The solution in DCM is then washed with HCl (2M, 3×30 mL) in order to remove all the amine components. The resulting DCM solution then only contains the byproduct, urea, acylated by the amino acid. The aqueous acid solution is then basified straightaway with KOH (5M, 40 mL), in order to adjust the pH to >12, and then washed with DCM (6×20 mL) until both phases become limpid. The recombined organic phases are washed with brine and dried on Na₂SO₄. After filtration and evaporation, 0.54 g of a limpid oil comprising the compound II.2 (43 mol %, 52 wt %, 280 mg; 0.88 mmol) and its derivative which has lost the Boc group (H₂NLeu-NH—CH₂—C(Me)₂—NHMe, MW=215.3 Da, 57 mol %, 48 wt %, 260 mg, 1.2 mmol) is obtained. This mixture is filtered on a silica column by using a gradient of EA:Cy:MeOH (10:7:0=>10:7:3, v:v:v), in order to obtain exclusively the product II.2 in the form of a colorless oil which solidifies over time (235 mg; 0.74 mmol, 13%). Unlike the NMR spectra of compound II.1, those of compound II.2 confirm the expected absence of diastereoisomers. The figures numbering the NMR resonances refer to the numbering indicated in the synthesis Scheme 6 for the corresponding atoms of the compound I.8.

$^1$H NMR (500 MHz, CDCl₃): δ=6.80 (s, br; 1H; NH$_{amide}$); 5.04 (~d, br; 7.7 Hz; 0.8H; NH$_{Boc}$); 4.12-4.08 (m; 1H; H-2); 3.26 (dd; 14.0 & 5.9 Hz; 1H; H-9); 3.17 (dd; 13.3 & 4.9 Hz; 1H; H-9'); 2.34 (s; 3H; 3×H-12); 2.14 (s, br; 1H; NH$_{aliphatic}$); 1.72-1.65 (m; 2H; H-4+H-3); 1.54-1.49 (m; 1H; H-3'); 1.46 (s; 9H; 9×H-8); 1.11 (s; 6H; 6×H-11); 0.96 (d; 3.7 Hz; 3H; 3×H-5); 0.95 (d; 3.6 Hz; 3H; 3×H-5') ppm.

$^{13}$C NMR (125 MHz, CDCl₃): δ=172.9 (C1); 155.8 (C6); 80.0 (C7); 53.7 (C10); 53.5 (C2); 46.6 (C9); 41.4 (C3); 28.4 (3×C8); 28.3 (C12); 24.9 (C4); 24.6 (2×C11); 23.0 (C5);

22.2 (C5') ppm. HSQC, COSY and jmod spectra were measured in order to confirm the assignment of the signals.

MS (ESI, positive mode): m/z 316.3: [MH]$^+$.

Preparation of the Compound I.8: By substantially applying the same procedure as used for preparing the compound I.7, HPQ (149 mg; 0.628 mmol) and the compound II.2 (198 mg; 0.627 mmol) are introduced, in order to prepare the compound I.8. The crude of the reaction is treated with piperazine in dry pyridine, in order to trap any HPQ chloroformate which would not have reacted with the amine. The aqueous treatment described earlier provides crude yellow oil (299 mg) which contains the compound I.8, some HPQ, and trace amounts of the product resulting from the reaction with piperazine. A portion of the crude (200 mg) is purified in the following way. The solid is treated with DCM (2×1 mL) and the soluble portion separated by decantation. The latter is then purified by silica column chromatography (gradient Cy:EA 3:1=>1:1, v:v) in order to obtain the compound I.8 as a dense, colorless powder and with very strong blue fluorescence (134 mg; 0.231 mmol; Total yield is then 55%).

$^1$H NMR (500 MHz, CDCl$_3$): δ=8.29 (d; 7.8 Hz; 1H; H-23); 7.91 (d; 7.3 Hz; 0.8H; H-18); 7.80-7.78 (m; 2.2H; H-25+H-16); 7.55-7.48 (m; 2H; H-24+H-26); 7.39-7.35 (m; 1H; H-17); 7.24 (d; 8.3 Hz; 1H; H-15); 6.84 (s, br; 0.8H; H$_{amide}$); 6.18 (s, br; 0.1H; H$_{amide}$); 5.60 (d; br; 6.8 Hz; 0.7H; NH$_{carbamate}$); 4.23-4.03 (m; 1H; H-2); 3.81-3.37 (m; 2H; 2×H-9); 3.05 (s; 3H; 3×H-12); 1.80-1.49 (m; 3H; H-4+2× H-3); 1.34 (s; 6H; 6×H-11); 1.23 (s; 9H; 9×H-8); 0.95 (d; 6.6 Hz; 3H; 3×H-5); 0.93 (d; 6.5 Hz; 3H; 3×H-5') ppm.

$^{13}$C NMR (125 MHz, CDCl$_3$): δ=173.8 (C1); 162.5 (C21); 155.8 (C6); 154.8 (C13); 150.7 (C20); 149.4 (C27); 149.2 (C14); 134.9 (C25); 132.3 (C16); 130.7 (C18); 127.9 (C24); 127.6 (C23); 127.2 (C26); 126.6 (C22); 126.4 (C17); 123.8 (C15); 121.1 (C19); 79.5 (C7); 60.9 (C10); 53.6 (C2); 46.5 (C9); 41.2 (C3); 32.7 (C12); 28.3 (3×C8); 25.3 (C4); 25.0 (C11); 24.9 (C11'); 23.2 (C5); 22.0 (C5') ppm.

HSQC and COSY spectra were measured in order to confirm assignment of the signals. The figures numbering the NMR resonances refer to the numbering indicated in the synthesis Scheme 6.

MS (ESI, positive mode): m/z 580.3: [MH]$^+$. MS (ESI, negative mode): m/z 578.3: [M-H]$^-$.

Preparation of the Compound I.2: 56 mg of I.8 (0.097 mmol) are treated with dry DCM (1.5 mL) and with TFA (1.5 mL) and the resulting solution is stirred at room temperature for one hour before all the volatile components are removed under reduced pressure. TLC analysis of the crude (Cy:EA:MeOH 1:1:1; revealed by UV analysis, ninhydrin and KMnO$_4$) proves the total consumption of the compound I.8 and the absence of HPQ. Nevertheless, chromatography of a silica column (gradient Cy:EA:MeOH 1:1:0=>1:1:1, v:v:v) is conducted in order to obtain the compound I.2 (a dense and colorless powder; 48 mg; 0.081 mmol; 84%). The figures numbering the NMR resonances refer to the numbering indicated in the synthesis Scheme 6.

MS (ESI, positive mode): m/z 480.2:[MH]$^+$. MS (ESI, negative mode): m/z 478.3: [M-H]$^-$.

$^1$H NMR (500 MHz; D$_2$O): δ=8.02 (d; 8.2 Hz; 1H; H-23); 7.81-7.77 (m; 1H; H-25); 7.64 (dd; 7.4 & 1.7 Hz; H-18); 7.60-7.56 (m; 2H; H-16+H-26); 7.50-7.47 (m; 1H; H-24); 7.40-7.37 (m; 1H; H-17); 7.24 (d; 8.2 Hz; 1H; H-15); 3.81 (t; 7.4 Hz; 1H; H-2); 3.41 (d, br; 13.4 Hz; 1H; H-9); 3.08-3.00 (m; 1H; H-9'); 2.93 (s; 3H; 3×H-12); 1.54-1.41 (m; 3H; H-4+2×H-3); 1.02-0.83 (m; 6H; 6×H-11); 0.81 (d, 4.9 Hz+d, 4.9 Hz; 3H+3H; 6×H-5) ppm.

$^{13}$C NMR (125 MHz; D$_2$O): δ=170.4 (C1); 164.4 (*C21); 154.5 (*C13); 151.6 (*C27); 148.3 (C14); 147.8 (*C20); 136.0 (C25); 132.9 (C16); 129.7 (C18); 128.1 (C24); 126.5 (C23); 126.2 (C26); 126.0 (*C22); 126.0 (C17); 123.3 (C15); 119.7 (C19); 59.4 (C10); 52.0 (C2); 45.9 (C9); 40.0 (C3); 32.1 (C12); 24.0 (C4); 23.8 (2×C11); 21.6 (C5), 21.2 (C5') ppm. HSQC, HMBC, COSY and udeft spectra (the latter for the five starred quaternary carbons which have very slow relaxation and then have very little signal; see Piotto et al, Magn. Reson. Chem. 2006 (44), 943-947), were measured in order to confirm the assignment of the signals.

MS (ESI, positive mode): m/z 480.2:[MH]$^+$. MS (ESI, negative mode): m/z 478.3: [M-H]$^-$.

EXAMPLE I.3

The substrate I.3 is synthesized as described above for the substrate I.1 by replacing the synthetic intermediate II.1 with the compound II.3 in Scheme 7 below. The diamine protected by a protective cbz group (14) is prepared by reduction of proline-amide protected by commercial cbz with borane BH$_3$, in a reflux of THF with a published yield of 74% (Wang, J., et al. Chem. Eur. J. (2006) 12, 4321-4332).

Scheme 7

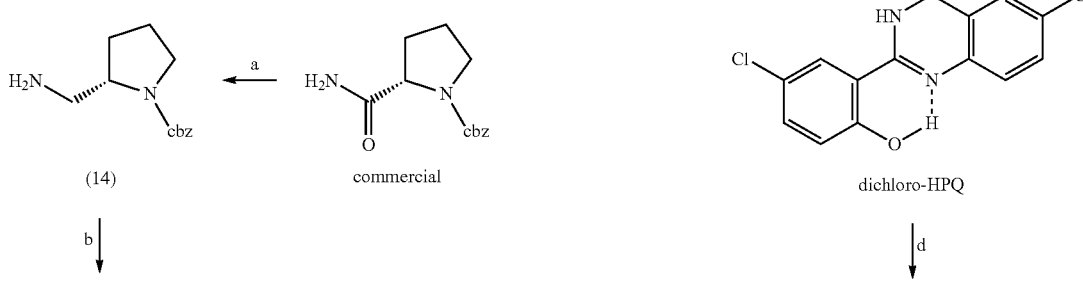

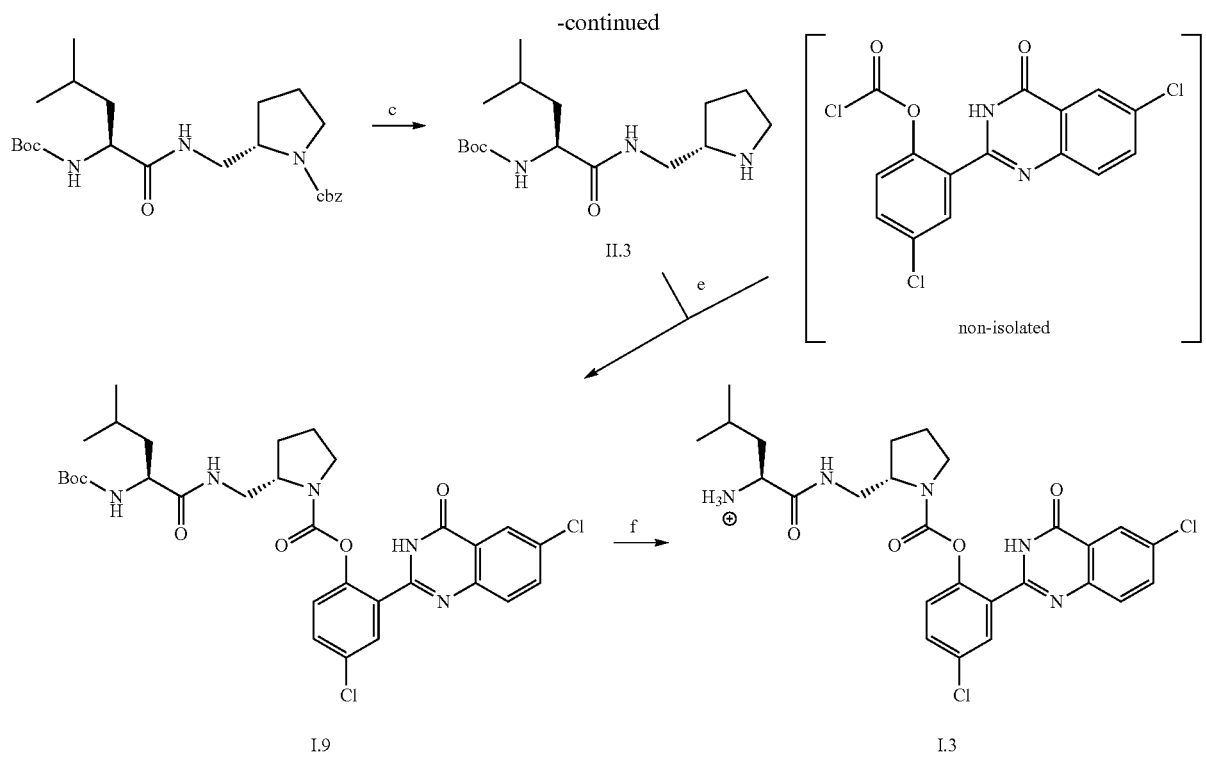
a) BH₃, THF reflux, 7h; b) BocLeuOH, DCC; c) H₂, Pd/C (10%), MeOH, 1h; d) triphosgen; e) TEA; (f) TFA.
EXAMPLE I.4
The probe I.4 is synthesized in a similar way to the probe I.1 with replacement of HPQ with the product 6.
EXAMPLE I.5
The probe I.5 is prepared as described in the following Scheme 8.
Scheme 8: Chemical Synthesis of example I.5
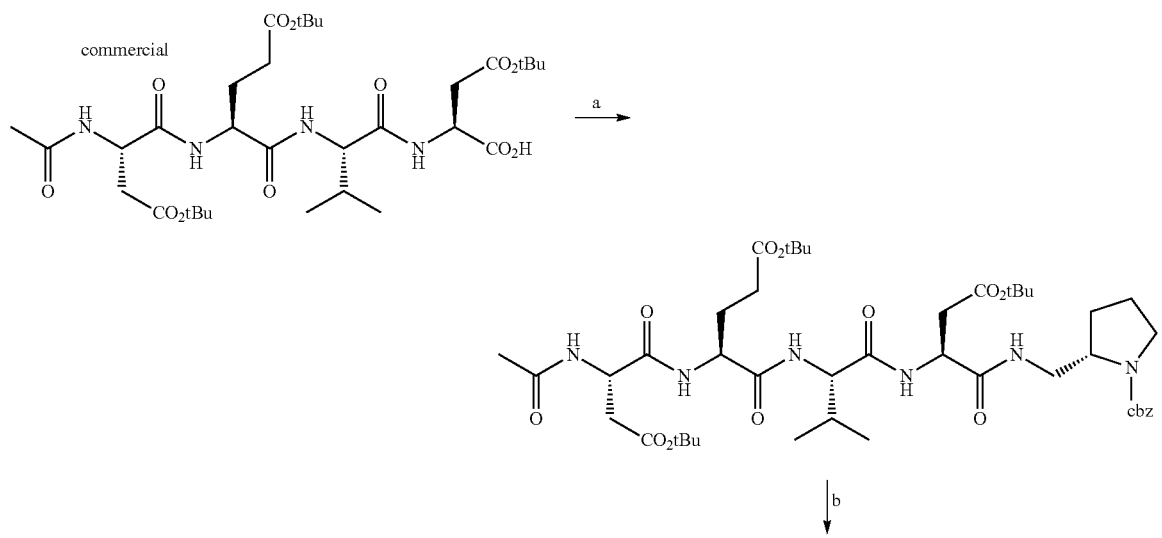

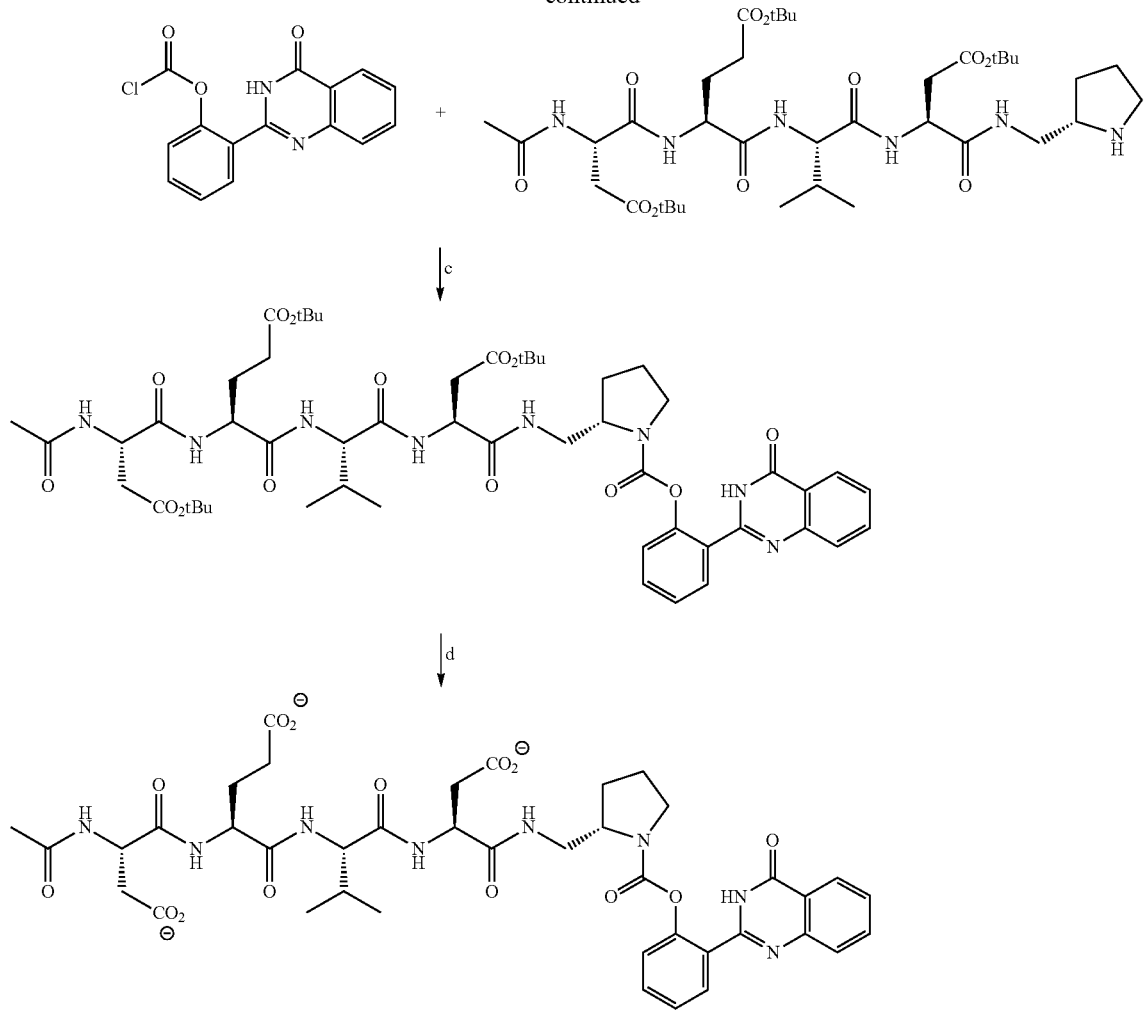

a) EDC/HOBt, diamine of Example 3; b) $H_2$, Pd/C (10%), MeOH, 1h; c) base; d) TFA/$CH_2Cl_2$.

EXAMPLE I.6

The probe I.6 is synthesized in the same way as the compound I.5 with replacement of the commercial protected peptide sequence Ac-DEVD, with the commercial protected peptide sequence Ac-HSSKLQ.

Enzymatic Tests

Preamble: Within the scope of the invention, upon applying the enzymatic tests, once the minimum, concentration allowing triggering of crystal nucleation is reached, a solid fluorophore may first be deposited on the walls of the receptacle (a well in a multi-well plate), before beginning to deposit on the bottom of the receptacle. The delay associated with the triggering of nucleation (≥10 mins) is well seen on the kinetic curves in the figures shown. The enzymatic tests carried out are illustrated with the appended figures.

FIG. 1 shows a typical image obtained in a scan mode which shows a spatial view of the intensity of the fluorescence triggered by the enzyme after 40 hours of incubation, in wells of a multi-well plate (Corning), which are illustrated in a grid with 6 columns (1-6) and 4 rows (A-D). The wells A1, A6, B2, C3 and D4 contain the PLA enzyme with a concentration of initially 209 μM of probe I.1; the wells B1, A2, C4 and D5 contain the enzyme PLA with a concentration of initially 80 μM of probe I.1; the wells A3, B4, C5 and D6 contain PLA enzyme with a concentration of initially 21.2 μM of probe I.1; the other wells do not contain any PLA but contain either 209 μM of probe I.1 (A4, B5, C6, D1, D3), or 80 μM of probe I.1 (A5, B6, C1, D2), or no probe I.1 (B3, C2). The signal is illustrated in a grey scale, black corresponding to a maximum of intensity.

FIG. 2 shows the image obtained in a scanning mode at a high resolution of another experiment carried out on the probe I.1, which shows the tendency of the probe activated by the enzyme (wells A2 and A3) of precipitating both in the centre of the wells but also on the edges. The well A1 only contains the buffer. The signal is illustrated in a grey scale, black being a maximum of intensity.

FIG. 3 shows the signals G(t) corresponding to the measured fluorescence in wells in the case of the probe I.2 at a concentration of 18 μM in the presence of PLA enzyme and at a concentration of 100 μM without any enzyme. For a series (I.2, 18 μM, with enzyme), the bold line shows the data kept after application of the algorithm elaborated for suppressing the five erratic values (arrows) of the original signal (non-bound triangles).

Figure 6:
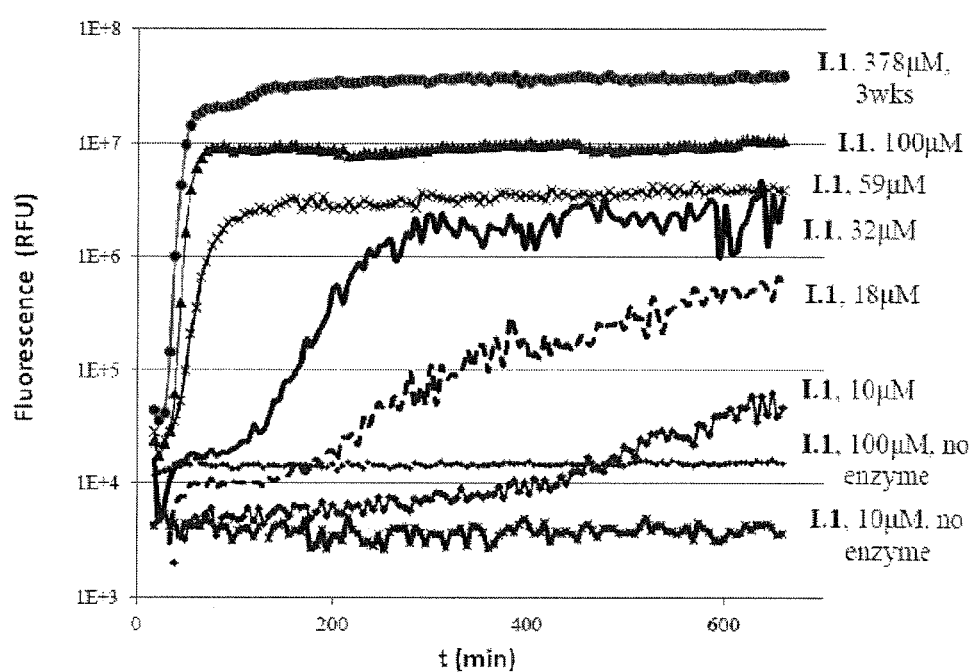

FIG. 6 shows on a logarithmic scale, the signals F(t) obtained according to the described procedure, for the compound I.1 freshly dissolved at various concentrations 10-100 µM, in the presence as well as in the absence of PLA enzyme, and for the same compound at 378 µM (calculated according to its original concentration upon its dilution) after three weeks of storage in an aqueous solution (<<3 wks>>) with the freshly added PLA.

Figure 7:
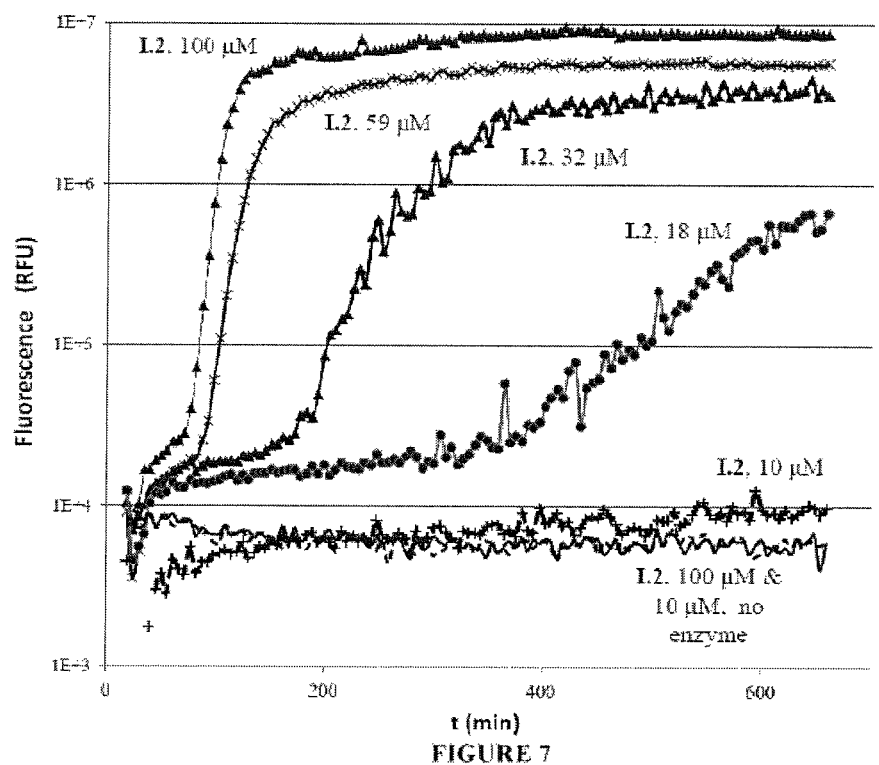

FIG. 7 shows on a logarithmic scale the signals F(t), obtained according to the described procedure, in the case of the freshly dissolved compound I.2 at various concentrations 10-100 µM, in the presence as well in the absence of a PLA enzyme.

Figure 8:
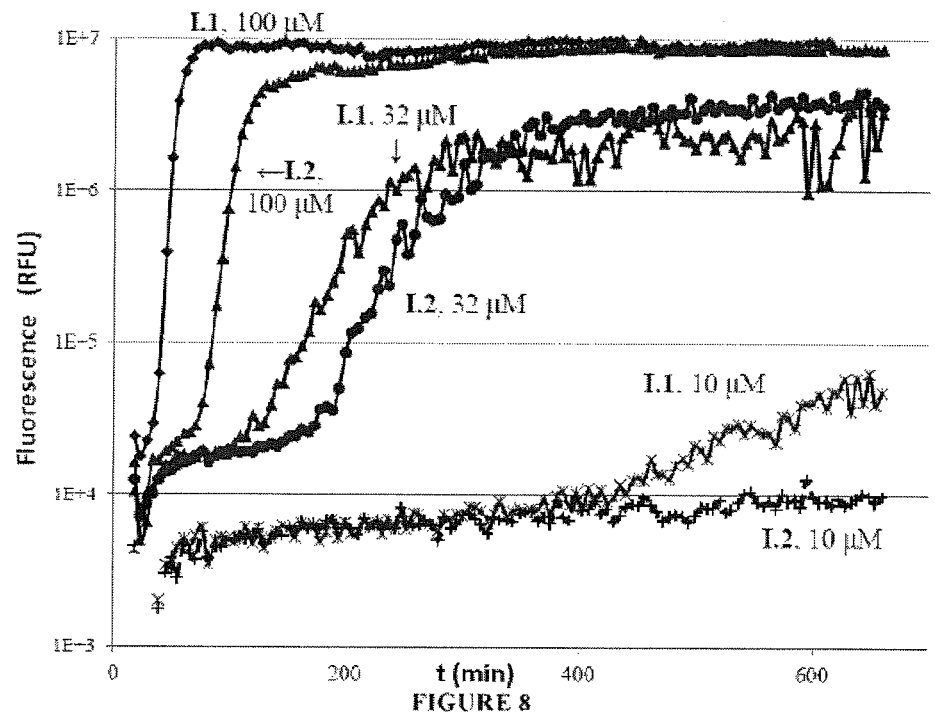

FIG. 8 comparatively shows on a logarithmic scale, the signals F(t) obtained according to the described procedure for the compounds I.1 and I.2 at concentrations of 100, 32 and 10 µM in the presence of PLA enzyme.

The probes I.1 and I.2 were evaluated by incubation with the target enzyme, microsomal leucine aminopeptidase (EC 3.4.11.2; "PLA"; commercial) in an in vitro medium in multi-well micro-plates designed for fluorescence readers. The probes were evaluated according to the following criteria:

Detection of the high fluorescence intensity generally by the presence of the enzymatic activity ("on"),
Detection of total absence ("quenched" or "off") of fluorescence in samples which do not contain the target enzyme (no intrinsic fluorescence),
Detection of the absence of any hydrolytic degradation of the probe over time demonstrating the robustness of the probes at pH 7 in an aqueous medium (no falsely positive signal),
Detection of the response rapidity to the presence of the enzymatic activity with which it is possible to rapidly attain a maximum signal,
Detection of the correlation of the measured signal with the concentration of the probe,
Detection of the strong photo-stability of the solid fluorophore generated under extended irradiation by the fluorescence reader.

The main tests were conducted at 25° C., in solutions buffered to pH 7.4 (physiological pH). Tests at 37° C. would have required the protection of the wells against premature evaporation, for example with the cover by a film which would have strongly reduced the sensitivity of the fluorescence measurement. A temperature of 25° C. was therefore preferred.

Reagents Used:
All the final solutions for the enzymatic tests were buffered to a pH varying from 7.4 to 7.6 (depending on the room temperature) with a 25 mM (total concentration) of Tris/Tris.HCl buffer, containing 11 mM of NaCl. The microsomal leucine aminopeptidase (EC 3.4.11.2) of pig kidney was purchased from Sigma (catalogue no. 069K7356) in the form of a suspension in ammonium sulfate (3.5 M) containing $MgCl_2$ (10 mM), with 3.5 mg·$mL^{-1}$ of protein contents and 10-40 U/mg of protein, as determined for the standard substrate, leucyl p-nitroanilide, and was stored in a fridge at 4° C. for a maximum of 40 days before its use. This enzyme suspension was initially diluted by a factor of 100 to 200 in 25 mM Tris/Tris.HCl buffer, homogenized, and left for one hour at room temperature before its use, since the incubation of the enzyme as described in the literature ((e.g. Beattie et al, Biochem. J. (1987) 242, 281-283) at 37° C., with or without $MgCl_2$ or $MnCl_2$, had not demonstrated superior consequent reactivity. The final concentration of the enzyme in the active wells was adjusted to a value of 3.5 µg$mL^{-1}$. The probes I.1 and I.2 were always dissolved, from solids stored in hermetically closed pill boxes, in MeOH (~5 mg$mL^{-1}$) before adding the Tris/Tris.HCl, before diluting them to the final concentrations used for the enzymatic tests.

Analyses Carried Out:
The analyses were carried out with reading of the fluorescence values, measured in RFU, versus time. The analyses were conducted in black polypropylene plates with 96 (Corning, Corning Inc.) or with 384 (Nunclon, Nunc Inc.) wells, and recorded on a microplate fluorimeter (Mithras LB940 from Berthold Technologies). This fluorimeter was used in a so-called repeated mode, where the fluorescence was measured with a reading, here selected to be 3 seconds per well, the excitation beam with a diameter of 4 mm being centered in the well. In spite of the tendency of the fluorophore once it is released, of depositing in a first phase on the walls of the well and not of falling straightaway to the bottom and to the middle of the well (see FIG. 2), the analyses in a repeated mode (only considering the fluorescence of the centers of the wells) were shown to be significant. It should be noted that this mode of use is close to the operation of optical high throughput screening by fluorescence, which is one of the applications envisioned for these types of probes. The images of FIG. 1 and FIG. 2 were acquired in a so-called scanning mode, where the excitation beam and the reader were moved, step by step, in order to cover each well notably including its edges. In the scanning mode, the wells were divided into a square read-out grid, typically covering the well with a resolution of 8×8 to 15×15 pixels, each of the pixels being read between 0.1 and 0.3 s. This scanning mode partly removes the errors and the read-out noise of the total fluorescence of the well subject to the repeated mode, subsequently to the tendency of the fluorophore once it is released of depositing a first phase on the walls. The scanning mode as implemented here is also slower and less suitable for qualitatively following reaction kinetics. It should be noted that this mode of use is close to the operation of cell counting, which is a second application envisioned for these types of probes.

Figure 1:
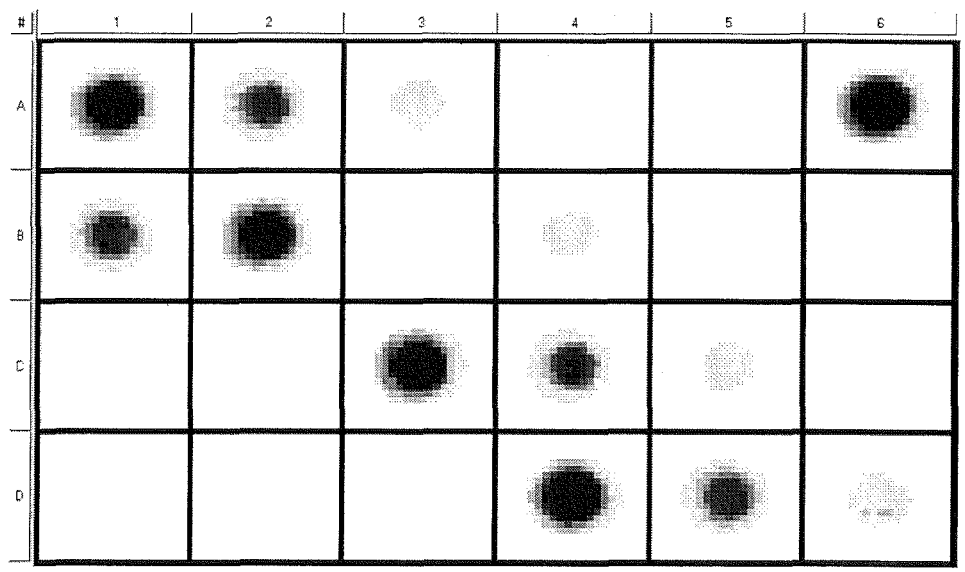
Figure 2:
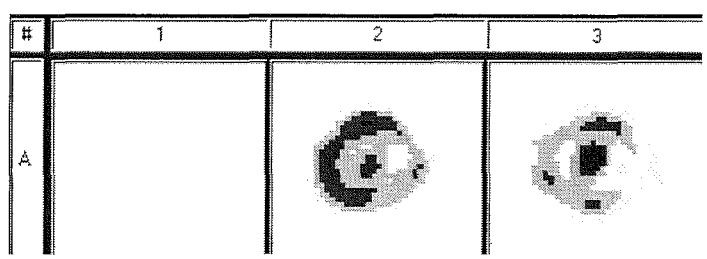

It is noticed in FIG. 1 that the observed fluorescence varies depending on the initial concentration in each well (the three sequences of wells, with an initial concentration of probe I.1 of 209 µM, 80 µM and 21 µM, may easily be localized), and that there is no comparable fluorescence in the other wells (the wells containing the probe without any enzyme at 209 µM and at 80 µM, are as invisible as the wells not containing any probe), which illustrates the quenched (OFF)-ON functionality of the probe, the absence of any intrinsic fluorescence of the probe, and the absence of any falsely positive signal due to spontaneous hydrolysis of the probe, even after 40 hours of incubation.

The excitation wavelength for the probes I.1 and I.2 (based on HPQ) was set to 355 nm, and the localized emission wavelength was set to 510 nm, since the fluorimeter used has filters of the bandpass type for selecting these wavelengths with a bandwidth of 14 nm for the excitation beam and of 10 nm for the emission one.

Procedure of the Acquisitions:

The enzyme was added last to the prepared wells. After adding the enzyme, the contents of the well were sucked up and released twice with a pipette, in order to homogenize as much as possible the mixture. This generated a delay from 5 to 20 minutes before the first acquisition, depending on the number of wells per acquisition, but this delay did not prevent the acquisition at the moment when the first wells started to exhibit fluorescence. The addition of the enzyme well by well was accomplished by observing the reading delay between the wells, so that the reaction times of each well were the same for each readout of the plate in order to allow comparison of the acquired data for different wells (in these experiments, there was a delay between 3 seconds and 20 seconds, between the readout of the neighboring wells, to be multiplied by up to 77 wells read by acquisition at a time t). Unless indicated otherwise, fluorescence values $A_{X,i}(t)$ of at least five wells, (I repetitions) for each sequence X of active conditions (concentration and nature of the substrate, enzyme concentration, . . . ) and at least three repetitions for each sequence of control conditions (for example no enzyme and/or no substrate) were measured in each procedure. The platelets were stirred between the readouts for about 10 seconds.

Pre-Treatment of the Data

The repeated mode acquires a function of fluorescence values of each well, measured in RFU versus time; these crude value functions are noted as $A_{X,i}(t)$ (the indexes indicating the repetition of the sequence X). The average, B(t), of the crude fluorescence values (in RFU) obtained for the sequence of (three or more) control wells containing the buffered solution and an amount of enzyme equal to the one used in the active wells, but without a substrate, is calculated. And then the functions $G^{*}_{X,i}(t)=A_{X,i}(t)-B(t)$ were calculated, in order to remove an environmental signal superposed on the measured signal stemming among other factors from the dispersion of light by the platelet, the enzyme and the buffer medium, from dispersion of light by the dust present in the air and on the surface of the wells. Next, the $G^{*}_{X,i}(t)$ were normalized in order to obtain the functions $G_{X,i}(t)=G^{*}_{X,i}(t) \times B(t=0)/B(t)$ for each well. This normalization allows comparison of the fluorescence values over time, by compensating a little for the effects such as the displacement of the calibration of the detector ("detector drift") or possible variations in the intensity emitted by the UV lamp during acquisitions which may last for more than 24 hours.

Figure 3:
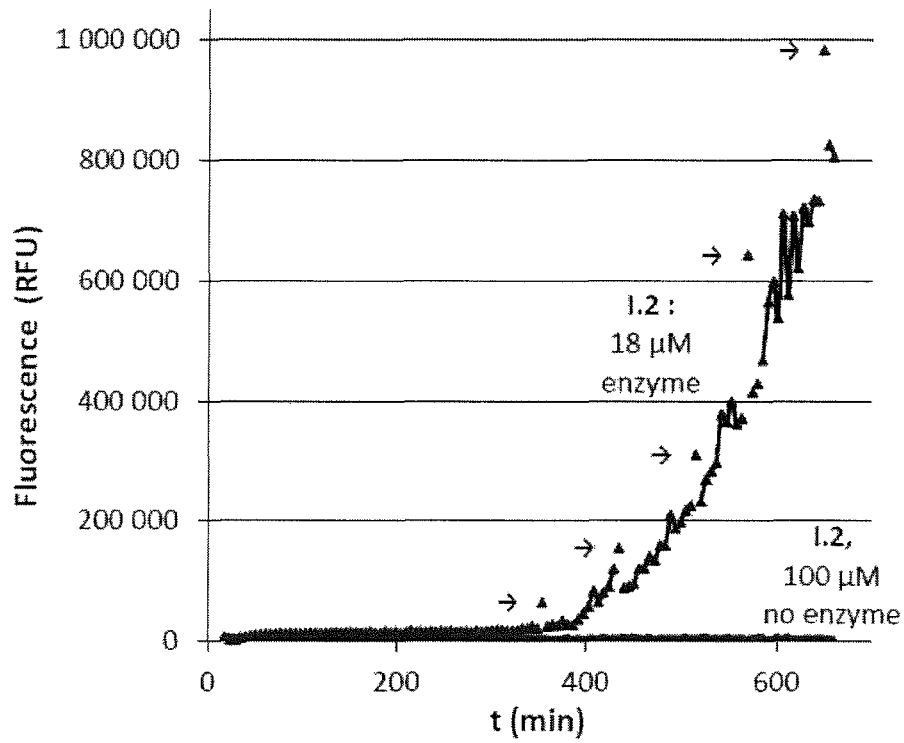

FIG. 3 shows that the probe I.2 does not degrade in the absence of enzyme (absence of any falsely positive signal), even at a high concentration, but it actually allows a very strong signal to be generated in the presence of an enzyme, and this even at a much lower concentration.

Erratic Data:

The crude data of each well were examined in order to study their consistency, since it was sometimes seen that one point (points designated by an arrow in FIG. 3) was very different from its neighbors, for example up to 300% of RFU more or less than the arithmetic mean of the neighboring values. It was considered that in such cases, these were not natural variations of the acquired signal, but erratic values due for example to the presence of dust particles which would have arrived on the analysis plate dispersing the light, and which would have been swept by the air drafts near the reader. Therefore, it was decided to abandon these points considered as erratic, while keeping the obtained total curve for the relevant well. A test was elaborated, in order to determine whether a point may be described as erratic or not.

For a point $G_{X,i}(t)$, an expected value, inversely weighted by the quantity of the neighboring values was calculated for obtaining $\mu_{X,i}(t)=[(3G_{X,i}(t-3)+2G_{X,i}(t-2)+2G_{X,i}(t+2)+3G_{X,i}(t+3))/10]$. The value, $\Delta_{X,i}(t)=[G_{X,i}(t)-\mu_{X,i}(t)]^{2}/(|\mu_{X,i}(t)|+|G_{X,i}(t)|)$ was then calculated. The points $G_{X,i}(t)$ corresponding to the largest values of $\Delta_{X,i}(t)$ were able to be rejected in decreasing order, and the values of new $\mu_{X,i}(t')$ of the neighboring points were recalculated until 5% of the obtained points of a series are rejected (for example the five arrowed points in FIG. 3). This method was adapted for values towards the end of the acquisition (which had to correspond to the fluorescence plateau) but was not applied to the three points of initial data, for fear of concealing a rapid increase of the signal corresponding to the activation of the probe. This method was not either applied to the regions of data in which the fluorescence values corresponded to a rapid non-linear increase. The curve obtained with this method, applied to the curve G(t) with the data points as triangles, is also illustrated in FIG. 3 in bold characters, showing the points (aimed by an arrow) which were removed.

Retained Data and Obtaining of Average Fluorescence Values $F_{X}(t)$:

In order to analyze the most consistent data, the data curves without any erratic points $G_{X,i}(t)$, of up to two of the repetitions i of each sequence X were rejected, with the conditions (1) that at least three repetitions for each sequence would always be kept and (2) the signal of a rejected well should have exceeded an arbitrary deviation threshold between its values and the values of the global average of the sequence $M_{X}(t)$. In order to evaluate a rejection, the average $Q_{X,i}$ of all the values of the function $|(G_{X,i}(t)-M_{X}(t))^{2}/M_{X}(t)|$ was first calculated; in order to reject a repetition i, the ratio $R_{i}=[Q_{X,i}/(\text{the average value of the five last points of }M(t))]$ had to be greater than 0.025. After thus having rejected for each sequence X the well i with the largest $Q_{X,i}$, the $M_{X}(t)$ and $Q_{X,i}$ were recalculated for re-evaluating the remaining $Q_{X,i}$, and the procedure was reapplied. It should be noted that this step does not intrinsically go against possible variations between neighboring values, $G_{X,i}(t)$ et $G_{X,i}(t')$ (this difference is comparable to a signal-to-noise ratio). The repetitions kept are marked as "acceptable" and for each retained sequence X of points, the values $G_{X,i}(t)$ of the retained functions were averaged, in order to obtain the series of fluorescence values $F_{X}(t)$ of each sequence of conditions X.

Acquired Data:

An acquisition for 11 hours in a repeated mode was undertaken (1) for demonstrating the stability of the probes I.1 and I.2, (2) for showing their minimum background fluorescence values, (3) for showing the significant signals triggered by the enzymatic activity, with a variable range of concentrations, (4) for obtaining the approximate action kinetics of the probes, and (5) for evaluating versus elapsed time, whether the signals obtained due to enzymatic activity could be considered as quantitative with this fast acquisition mode. Each of the probes was tested in a range of concentrations from 10 µM to 100 µM; for each of these probes, two series of controls of stability were measured, one at 100 µM and one at 10 µM, in order to demonstrate the absence of any falsely positive signal. A series of control measurements of background fluorescence was carried out, with wells containing some enzyme in the standard buffer without any probe. A last series of measurements was conducted by using a solution of probe I.1 prepared three weeks beforehand ("3 wks"), in order to obtain another estimation of the robustness of this probe towards spontaneous hydrolysis in practice. Each readout lasted for 3 seconds per well. The obtained results are shown in graphic format in FIGS. 4 to 8.

Figure 4:
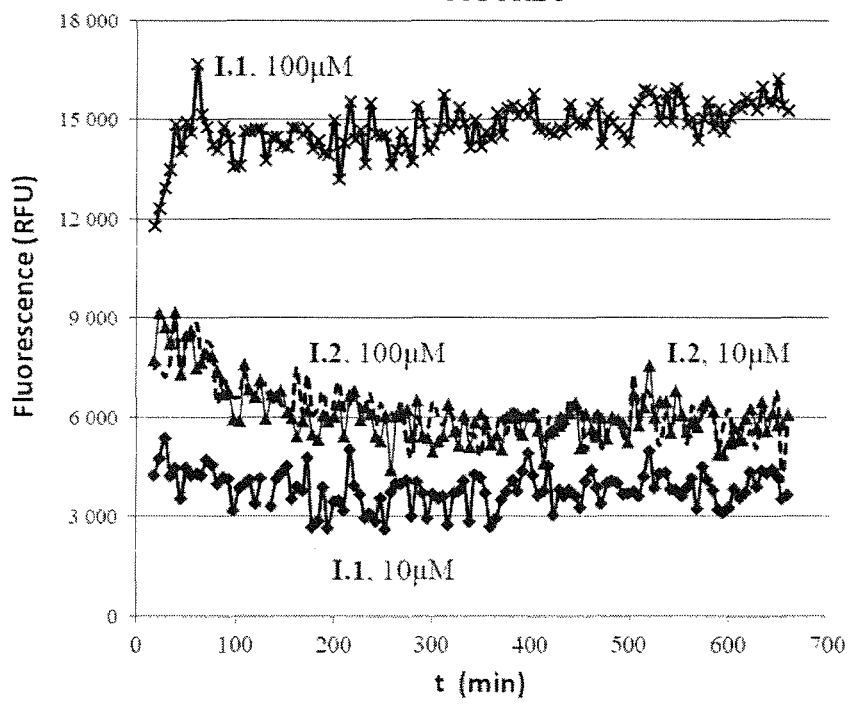
FIG. 4 shows the time-dependent change of fluorescence signals F(t) versus time, obtained according to the described procedure, in the absence of any PLA enzyme in aqueous solutions buffered to pH~7.6, of the compound I.1 at 10 µM and at 100 µM, and of the compound I.2 at 10 µM and at 100 µM (both of the two latter signals are almost entirely superposed).

FIG. 4 shows the total stability to spontaneous hydrolysis of the substrate according to the invention and the absence of any falsely positive signal for the probes I.1 and I.2 during the 11 h of acquisition. As a comparison, probes published earlier by one of the inventors (Zhang, Waibel and Hasserodt, Chem. Eur. J. 2010, 16, 792) showed, under similar conditions for a probe at 38 µM, a signal increase of the control wells in the absence of an enzyme of the order of 10-15% for 150 minutes (therefore a falsely positive signal). With the probes according to the invention, NO signal increase relatively to the noise of the signals is seen even at a concentration of 100 µM and for 660 minutes.

The intrinsic fluorescence values for the probe I.2 (counter-ion used: $CF_3CO_2^-$) seem to be insensitive to its concentration in solution, while the fluorescence values for the probe I.1 (counter-ion used: pTsO$^-$) show some dependency on its concentration.

Figure 5:
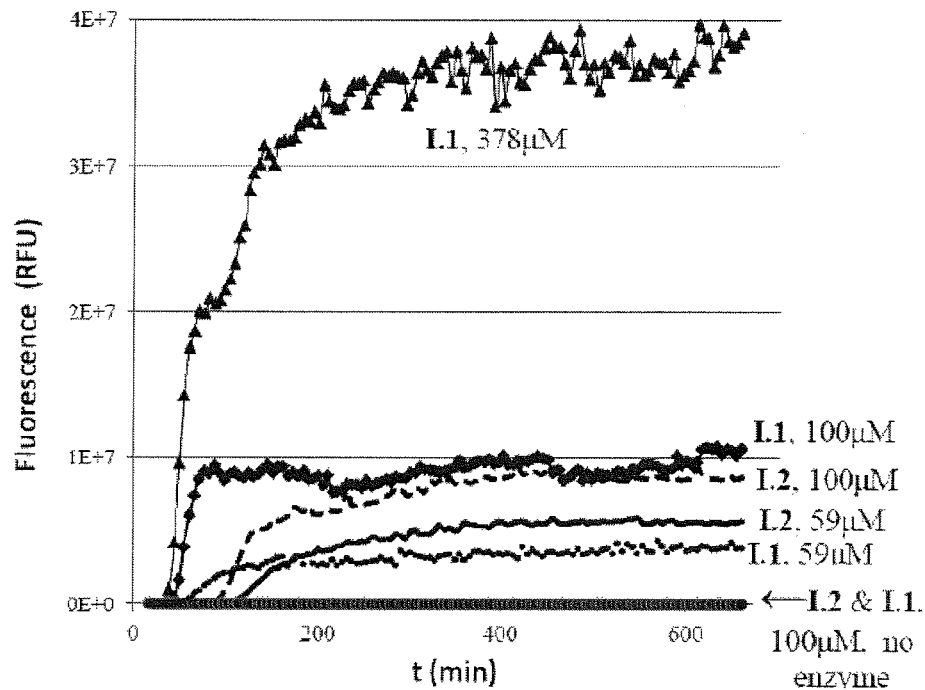
FIG. 5 shows on a linear scale the signals F(t) obtained according to the prescribed procedure, for the compounds I.1 (at 378 µM, 100 µM and 59 µM) and I.2 (à 100 µM and 59 µM) in the presence of PLA enzyme, and for the same compounds each at 100 µM, but without PLA (controls).

FIG. 5 shows the intense fluorescence signal which is rapidly obtained in the presence of the enzyme, with the compounds I.1 and I.2 at different concentrations and shows the weakness of the intrinsic fluorescence values as compared with the latter (observed for probes in the absence of an enzyme). It should be noted that the delay for obtaining an intense increase in the signal is very short: it is of about 10 minutes for the reasons discussed in the preamble but is generally less than 100 minutes.

FIG. 6 shows the obtaining of the intense fluorescence signal, rapidly obtained with compound I.1 in the presence of the enzyme, while very small background fluorescence values are observed for the same probe in the absence of an enzyme. It should be emphasized that 500 minutes onwards, even with the lowest concentration of 10 µM of compound I.1, a signal is obtained which cannot be confused with the background fluorescence even obtained for the series of measurements carried out at 100 µM, corresponding to ten times its probe concentration but without any enzyme for activating it. Moreover, the signals, once the plateau is reached, do not decrease over time: the irradiation levels of the instrument therefore are not sufficient for causing localizable photo-degradation.

The results shown in the curves of FIG. 7 in the case of the compound I.2 are comparable, and therefore also satisfactory.

FIG. 8 shows the kinetic differences in the triggering of the signal for the probes I.1 and I.2 versus the concentration. It will be noted that the values of the fluorescence plateaus for both compared probes at identical concentrations (100 µM and 32 µM) are the same, as expected for total activation of the probe present in the well.

The $t_{1/2}$ times observed in the procedure used for the probes I.1 and I.2 incubated with the enzyme corresponding to half of the maximum observed signals during the 11 hours of acquisition were calculated and are shown in Table 2. These values give an estimation of the rapidity of action of the probes with the low enzyme concentrations used.

TABLE 2

| | Values $t_{1/2}$ (mins) |
|---|---|
| I.1, 378 µM « 3 wks» | 71 |
| I.1, 100 µM | 55 |
| I.2, 100 µM | 125 |
| I.1, 59 µM | 93 |

TABLE 2-continued

| | Values $t_{1/2}$ (mins) |
|---|---|
| I.2, 59 µM | 162 |
| I.1, 32 µM | 237 |
| I.2, 32 µM | 344 |
| I.1, 18 µM | 499 |
| I.2, 18 µM | 460 |
| I.1, 10 µM | 520 |
| I.2, 10 µM | 533 |

By using the fluorescence values "of the plateau" (maximum values and not changing over time) measured with probe concentrations of 378 µM to 32 µM (after 200-400 min until the end of the acquisition), the signal plateau/concentration ratio for each series of wells was evaluated. A variation of the order of only 20% was seen between the ratio values obtained for series of different measurements, which shows a correlation between the measured signal for the test with the enzyme, and the initial concentration of the probe, when the fluorophore portion of these probes is the same. By using the average value of the obtained ratios, the initial concentration of the probes in the active wells was estimated. The values obtained are shown in Table 3. The thereby estimated values are quite close to the actual values. In the case of concentrations at 18 µM and at 10 µM, the plateaus not having been reached, the calculated concentrations prove to be underestimated as expected.

TABLE 3

| | Signal/Conc. (RFU µM$^{-1}$) | Predicted Conc. (µM) |
|---|---|---|
| I.1, 378 µM, 3 wks. | 98684 | 419 |
| I.1, 100 µM | 95711 | 108 |
| I.2, 100 µM | 87269 | 98 |
| I.1, 59 µM | 63054 | 42 |
| I.2, 59 µM | 95096 | 63 |
| I.1, 32 µM | 72794 | 26 |
| I.2, 32 µM | 110289 | 40 |
| I.1, 18 µM | | 6 |
| I.2, 18 µM | | 6 |
| I.1, 10 µM | | 0 |
| I.2, 10 µM | | 1 |
| Average ratio | 88985 | |

The invention claimed is:
1. A peptidase substrate of formula (I):

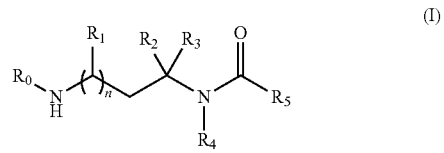

wherein:
R$_0$ is a peptidyl or amino acid group bound to the NH group via its carboxy-terminal end,
n is 0 or 1,
R$_1$ is a hydrogen atom or a side chain of a natural amino acid,
R$_5$ is a phenoxy-containing moiety, the corresponding phenolic form of which belongs to the excited state intramolecular proton transfer (ESIPT) class of fluorophores, $R_2$, $R_3$ and $R_4$ are defined as follows:

$R_2$ is a $(C_1-C_4)$alkyl group or a hydrogen atom, $R_3$ is a $(C_1-C_4)$alkyl group, and $R_4$ is a $(C_1-C_4)$alkyl group; or else $R_2$ is a $(C_1-C_4)$alkyl group or a hydrogen atom and $R_3$ and $R_4$ are bound together and form with the carbon and nitrogen atoms to which they are bound an aliphatic heterocycle, this heterocycle may be substituted with an ammonium, carboxylate or sulfonate group allowing an increase in water-solubility of the substrate; or else $R_4$ is a $(C_1-C_4)$alkyl group and $R_2$ and $R_3$ are bound together and form with the carbon atom to which they are bound an aliphatic carbocycle, or in a form of any optical isomer or diastereomer, or in a form of a mixture of optical isomers or diastereomers in any proportions.

2. The peptidase substrate according to claim 1, characterized in that $R_2$=H and $R_3$ and $R_4$ are bound together and form a sequence —$(CH_2)_m$— with m=3, 4 or 5.

3. The peptidase substrate according to claim 1, characterized in that $R_2$, $R_3$ and $R_4$, either identical or different, represent a $(C_1-C_4)$alkyl group.

4. The peptidase substrate according to claim 3, characterized in that $R_2$=$R_3$=$R_4$=$R_4$=—$CH_3$.

5. The peptidase substrate according to claim 1, characterized in that $R_5$ is selected from groups of formula (A):

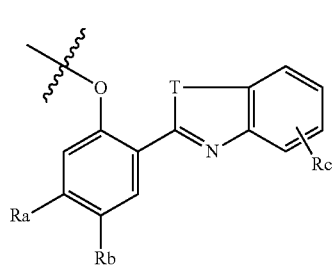

(A)

wherein:

T is —NH—C(O)—, —S—, —O—, —NH, N-alkyl or N-aryl,

Ra is selected from the group consisting of hydrogen, —CN and —COORd, wherein Rd represents a $(C_1-C_4)$ alkyl group or else Ra is —CONReRf, wherein Re and Rf, either identical or different, represent a hydrogen or a $(C_1-C_4)$alkyl group, or else Ra is —$CF_3$, or a 2-oxazolyl, 2-thiazolyl, 2-imidazolyl (either benzo-fused or not), 4-pyrimidinon-2-yl or quinazolinon-2-yl, Rb is hydrogen, a chlorine atom, —OH, —$NH_2$,— NRgRh or —ORg, with Rg and Rh either identical or different, which represent a $(C_l-C_4)$alkyl group, or else Ra and Rb are bound together so as to form a saturated or unsaturated, substituted or non-substituted hydrocarbon chain comprising 4 or 5 members, optionally interrupted with one or several heteroatoms selected from N, S and O, Rc is hydrogen, Br, Cl, I, F, or

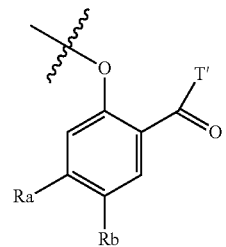

wherein:

T' is $NH_2$, OH, an aryl, a $(C_1-C_4)$alkyl, SH, NHR, OR, $NR_2$, SR, R being a $(C_1-C_4)$alkyl or an aryl, Ra is selected from the group consisting of hydrogen, —CN and —COORd, wherein Rd represents a $(C_1-C_4)$ alkyl group or Ra is —CONReRf, wherein Re and Rf, either identical or different, represent a hydrogen or a $(C_1-C_4)$alkyl group, or else Ra is —$CF_3$, or a 2-oxazolyl, 2-thiazolyl, 2-imidazolyl (either benzo-fused or not), 4-pyrimidinon-2-yl, or quinazolinon-2-yl, Rb is hydrogen, a chlorine atom, —OH, —$NH_2$, —NRgRh or —ORg, with Rg and Rh either identical or different, which represent a $(C_1-C_4)$alkyl group, or else Ra and Rb are bound together so as to form a saturated or unsaturated, substituted or non-substituted hydrocarbon chain comprising 4 or 5 members, optionally interrupted with one or several heteroatoms selected from N, S and O.

6. The peptidase substrate according to claim 1, of formula (IA):

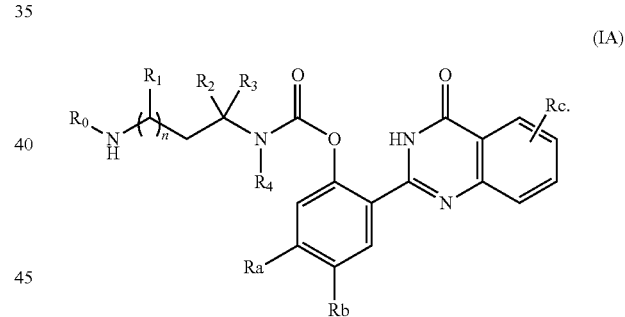

(IA)

7. The peptidase substrate according to claim 5 characterized in that Ra=Rb=Rc=H or Ra=H, Rb=Rc=Cl.

8. The peptidase substrate according to claim 5 characterized in that Ra and Rb are bound together, so that the substrate according to the invention fits formula (IA') or (IB'):

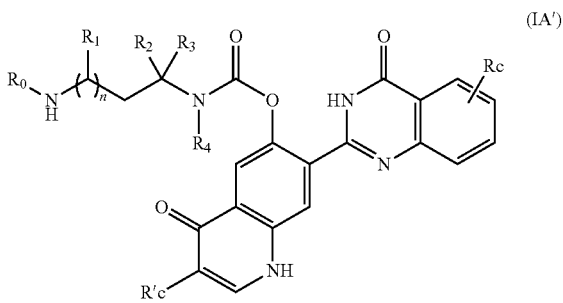

(IA')

-continued

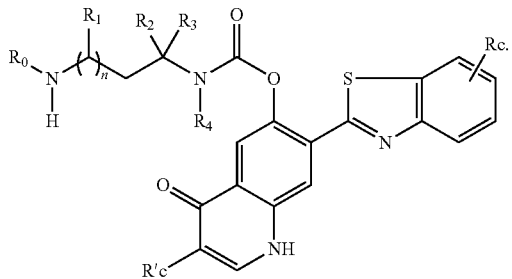

(IB')

9. The peptidase substrate according to claim 1, characterized in that $R_0$ represents an amino acid or a peptidyl group including at most 10, amino acids in which the amino acids are either identical or different and are selected from natural amino acids, and the N-terminal end may be non-substituted or substituted with an acyl group —COR", R" being a $(C_1-C_6)$alkyl group or a O—$(C_1-C_6)$alkyl group.

10. The peptidase substrate according to claim 1, characterized in that n=0.

11. The peptidase substrate according to claim 1, characterized in that n=1 and $R_1$ represents the side chain of a natural amino acid.

12. The peptidase substrate according to claim 1, characterized in that the peptidyl or amino acid group $R_0$ is a substrate for leucine aminopeptidase, caspase-3, HIV-1 peptidase, renin, thrombin, tryptase, cathepsin K, IACE plasmepsins I or II, β-secretase or the prostate-specific antigen.

13. A method for detecting the presence of a catalytically active peptidase comprising the steps of:

putting a sample suspected of containing said peptidase in contact with a substrate according to claim 1;

applying suitable conditions for allowing the formation of a fluorescent precipitate by cleavage of the covalent bond between NH and $R_0$, followed by cleavage of the —C(O)—$R_5$ bond following cyclization into a cyclic urea; and quantitatively or qualitatively analyzing said fluorescent precipitate.

14. The method according to claim 13, wherein the analysis of the fluorescent precipitate comprises the steps of:

exposing the fluorescent precipitate to a light source capable of producing light at an absorption wavelength of the fluorescent precipitate; and detecting the fluorescence of the precipitate.

* * * * *